(12) United States Patent
Cardinale et al.

(10) Patent No.: US 10,675,020 B2
(45) Date of Patent: Jun. 9, 2020

(54) APPLICATOR INSTRUMENTS FOR DISPENSING SURGICAL FASTENERS HAVING ARTICULATING SHAFTS AND ARTICULATION CONTROL ELEMENTS

(71) Applicant: Ethicon, Inc., Somerville, NJ (US)

(72) Inventors: Michael Cardinale, Morristown, NJ (US); Danial Paul Ferreira, Milford, CT (US); Doug Souls, Andover, NJ (US); Simon Cohn, Lebanon, NJ (US); Jianxin Guo, Livingston, NJ (US)

(73) Assignee: Ethicon, Inc., Somerville, NJ (US)

( * ) Notice: Subject to any disclaimer, the term of this patent is extended or adjusted under 35 U.S.C. 154(b) by 179 days.

(21) Appl. No.: 16/005,171

(22) Filed: Jun. 11, 2018

(65) Prior Publication Data

US 2018/0289367 A1    Oct. 11, 2018

Related U.S. Application Data

(63) Continuation of application No. 14/943,165, filed on Nov. 17, 2015, now Pat. No. 10,292,702.

(51) Int. Cl.
*A61B 17/29* (2006.01)
*A61B 17/068* (2006.01)
(Continued)

(52) U.S. Cl.
CPC .... *A61B 17/0682* (2013.01); *A61B 17/00234* (2013.01); *A61B 17/068* (2013.01);
(Continued)

(58) Field of Classification Search
CPC .............. A61B 17/0682; A61B 17/068; A61B 17/00234; A61B 17/064;
(Continued)

(56) References Cited

U.S. PATENT DOCUMENTS

| 3,740,994 A | 6/1973 | DeCarlo, Jr. |
| 4,471,780 A | 9/1984 | Menges et al. |

(Continued)

FOREIGN PATENT DOCUMENTS

| EP | 0596213 | 5/1994 |
| EP | 2044893 | 4/2009 |

OTHER PUBLICATIONS

International Search Report issued by the International Searching authority in International Application No. PCT/US2016/061091, dated Feb. 27, 2017, 4 pages.

(Continued)

*Primary Examiner* — Robert F Long

(57) ABSTRACT

An applicator instrument for dispensing surgical fasteners includes a handle and an articulating shaft extending from the handle including proximal and distal shaft sections and an articulating joint interconnecting the proximal and distal shaft sections. The proximal shaft section has a proximal outer tube and a proximal inner member, and the distal shaft section includes a distal outer tube and a distal inner member. An incompressible member interconnects the proximal and distal inner members to form an inner shaft member having a fixed length. Distal movement of the proximal outer tube relative to the proximal inner member articulates the distal shaft section relative to the proximal shaft section via the articulating joint. As the articulating shaft moves between a straight configuration and an articulated configuration the distance between a distal-most end of the distal outer tube and the handle changes while the length of the inner shaft member remains fixed.

20 Claims, 23 Drawing Sheets

(51) Int. Cl.
*A61F 2/00* (2006.01)
*A61B 17/00* (2006.01)
A61B 17/064 (2006.01)
A61B 90/00 (2016.01)

(52) U.S. Cl.
CPC .......... *A61F 2/0063* (2013.01); *A61B 17/064* (2013.01); *A61B 2017/00314* (2013.01); *A61B 2017/00323* (2013.01); *A61B 2017/2927* (2013.01); *A61B 2090/067* (2016.02); *A61B 2090/0811* (2016.02); *A61F 2002/0072* (2013.01)

(58) Field of Classification Search
CPC .. A61B 2017/00323; A61B 2017/2927; A61B 2090/067; A61B 2090/0811; A61B 2017/00314; A61F 2/0063; A61F 2002/0072; A61F 2002/072
USPC ........... 227/175.1–182.1; 606/139, 142, 143, 606/205, 208
See application file for complete search history.

(56) References Cited

U.S. PATENT DOCUMENTS

| | | | |
|---|---|---|---|
| 4,478,220 A | 10/1984 | DiGiovanni et al. | |
| 5,203,864 A | 4/1993 | Phillips | |
| 5,290,297 A | 3/1994 | Phillips | |
| 5,470,010 A | 11/1995 | Rothfuss et al. | |
| 5,514,157 A | 5/1996 | Nicholas et al. | |
| 5,582,616 A | 12/1996 | Bolduc et al. | |
| 5,601,573 A | 2/1997 | Fogelberg et al. | |
| 5,662,662 A * | 9/1997 | Bishop ................ | A61B 17/0684 227/175.1 |
| 5,743,456 A * | 4/1998 | Jones ................. | A61B 17/0684 227/176.1 |
| 5,792,165 A | 8/1998 | Klieman | |
| 5,797,536 A * | 8/1998 | Smith ................ | A61B 17/0682 227/175.1 |
| 5,810,882 A | 9/1998 | Bolduc et al. | |
| 5,820,009 A * | 10/1998 | Melling ........... | A61B 17/07207 227/176.1 |
| 5,830,221 A | 11/1998 | Stein et al. | |
| 5,833,700 A | 11/1998 | Fogelberg et al. | |
| 5,921,997 A | 7/1999 | Fogelberg et al. | |
| 7,485,124 B2 | 2/2009 | Kuhns et al. | |
| 7,887,553 B2 | 2/2011 | Lehman et al. | |
| 8,006,365 B2 | 8/2011 | Levin et al. | |
| 8,087,142 B2 | 1/2012 | Levin et al. | |
| 8,216,272 B2 | 7/2012 | Shipp | |
| 8,282,670 B2 | 10/2012 | Shipp | |
| 8,308,738 B2 | 11/2012 | Nobis et al. | |
| 8,474,679 B2 | 7/2013 | Felix | |
| 8,562,592 B2 | 10/2013 | Conlon et al. | |
| 8,579,920 B2 | 11/2013 | Nering et al. | |
| 8,728,098 B2 | 5/2014 | David et al. | |
| 8,728,099 B2 | 5/2014 | Cohn et al. | |
| 8,783,541 B2 * | 7/2014 | Shelton, IV ......... | A61B 17/064 227/175.1 |
| 8,894,669 B2 | 11/2014 | Nering et al. | |
| 8,920,439 B2 | 12/2014 | Cardinale et al. | |
| 8,926,598 B2 | 1/2015 | Mollere et al. | |
| 9,848,872 B2 * | 12/2017 | Smith .............. | A61B 17/07207 |
| 2005/0085830 A1 | 4/2005 | Lehman et al. | |
| 2007/0175949 A1 | 8/2007 | Shelton | |
| 2008/0083809 A1 | 4/2008 | Scirica | |
| 2009/0198272 A1 | 8/2009 | Kerver et al. | |
| 2010/0204717 A1 | 8/2010 | Knodel | |
| 2010/0211053 A1 | 8/2010 | Ross | |
| 2010/0312258 A1 | 12/2010 | Shipp | |
| 2011/0036890 A1 | 2/2011 | Ma | |
| 2011/0275901 A1 | 11/2011 | Shelton | |
| 2012/0199632 A1 | 8/2012 | Spivey | |
| 2012/0271285 A1 | 10/2012 | Sholev et al. | |
| 2013/0037596 A1 | 2/2013 | Bear | |
| 2013/0119108 A1 | 5/2013 | Altman et al. | |
| 2013/0303845 A1 | 11/2013 | Skula et al. | |
| 2013/0304091 A1 | 11/2013 | Straehnz et al. | |
| 2014/0236173 A1 * | 8/2014 | Scirica ............. | A61B 17/07207 606/130 |
| 2014/0276967 A1 | 9/2014 | Fischvogt | |
| 2015/0001272 A1 | 1/2015 | Sniffin et al. | |
| 2015/0005748 A1 | 1/2015 | Sniffin et al. | |
| 2015/0005788 A1 | 1/2015 | Sniffin et al. | |
| 2015/0005789 A1 | 1/2015 | Sniffin et al. | |
| 2015/0073439 A1 * | 3/2015 | Dannaher .......... | A61B 17/1285 606/142 |
| 2015/0119918 A1 | 4/2015 | Blase et al. | |
| 2015/0230791 A1 * | 8/2015 | Smith .............. | A61B 17/07207 227/175.2 |
| 2015/0320437 A1 * | 11/2015 | Worrell .......... | A61B 17/320068 606/169 |
| 2018/0368839 A1 * | 12/2018 | Shelton, IV ............ | B22F 3/225 |

OTHER PUBLICATIONS

Written Opinion of the International Searching authority issued in International Application No. PCT/US2016/061091, dated Feb. 27, 2017, 10 pages.

* cited by examiner

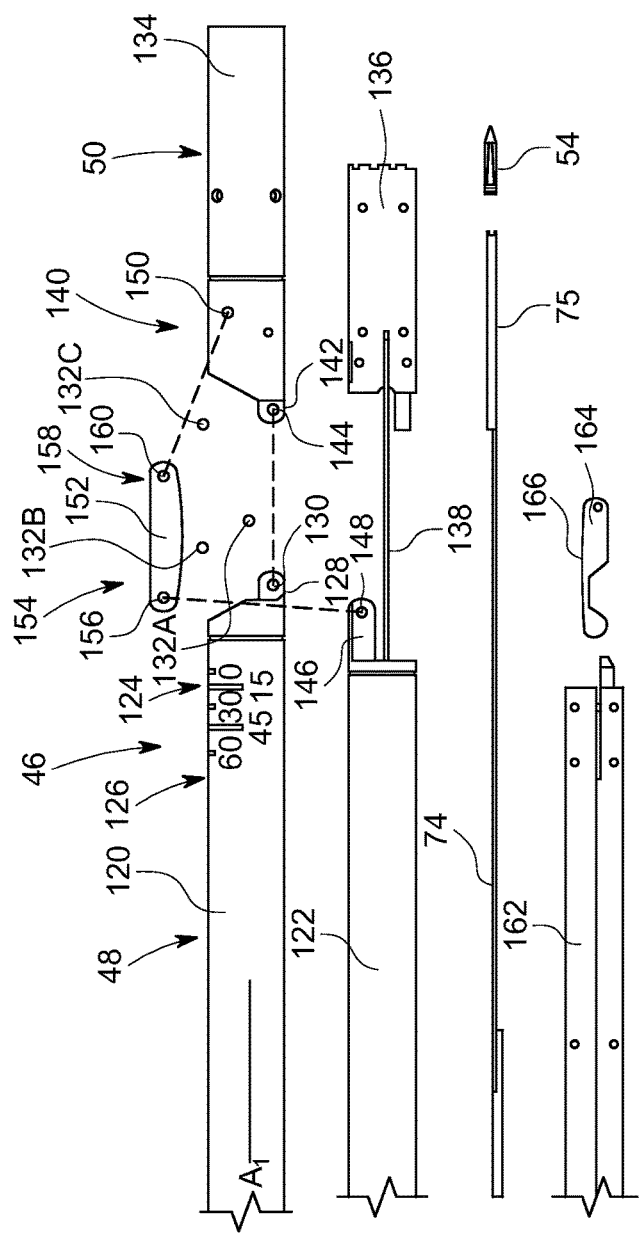
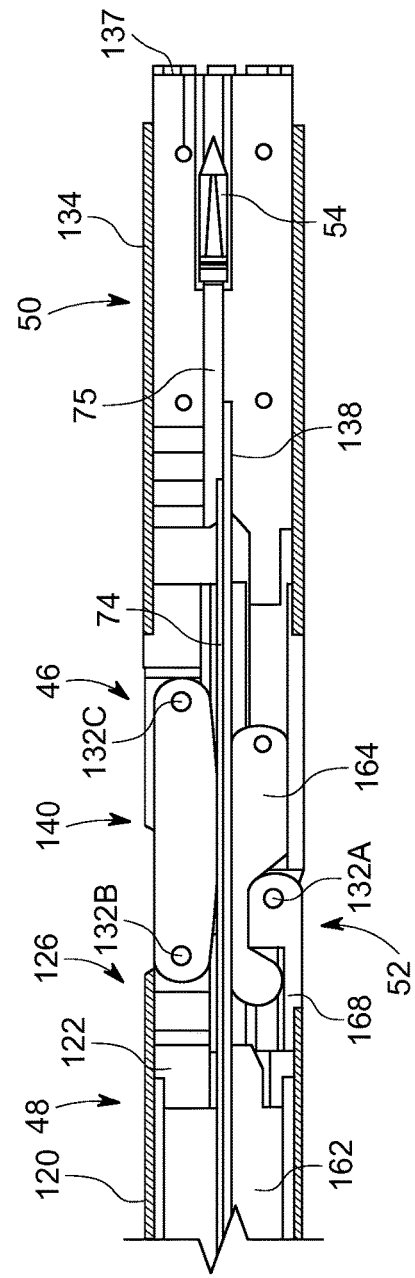
FIG. 8A
FIG. 8B

APPLICATOR INSTRUMENTS FOR DISPENSING SURGICAL FASTENERS HAVING ARTICULATING SHAFTS AND ARTICULATION CONTROL ELEMENTS

CROSS-REFERENCE TO RELATED APPLICATIONS

The present patent application is a continuation of U.S. patent application Ser. No. 14/943,165, filed Nov. 17, 2015, published on May 18, 2017 as US 2017/0135693, now allowed, the disclosure of which is hereby incorporated by reference herein.

BACKGROUND OF THE INVENTION

Field of the Invention

The present patent application generally relates to applicator instruments for dispensing surgical fasteners, and more specifically relates to applicator instruments, systems and methods that use articulating shafts for deploying surgical fasteners.

Description of the Related Art

A hernia is a condition where a small loop of bowel or intestine protrudes through a weak place or defect within the abdominal muscle wall or groin of a patient. This condition commonly occurs in humans, particularly males. Hernias of this type may result from a congenital defect whereby the patient is born predisposed with this condition, prior abdominal surgery, or may be caused by straining or lifting heavy objects. Heavy lifting may be known to create a large amount of stress upon the abdominal wall and can cause a rupture or tearing at a weak point of the abdominal muscle to create the defect or opening. In any case, the patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution to the above-described problem may be surgery. During a surgical procedure, the defect is accessed and carefully examined, either through an open incision or endoscopically through an access port such as a trocar. In either case, careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the defect, and attaching the mesh patch to the abdominal wall or inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal most staple from the stack, to hold the remainder of the spring loaded stack, and may be used to feed the distal most staples into the staple forming mechanism. Feeding mechanisms of this type are found in U.S. Pat. No. 5,470,010 to Rothfuss et al., and in U.S. Pat. No. 5,582,616, also to Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both to Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos. 5,601,573; 5,833,700; and U.S. Pat. No. 5,921,997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A valving mechanism may be also required to separate the distal-most clip from the stack and to hold the stack stationary as the distal most clip may be applied onto a vessel. Whereas the Fogelberg et al. references teach a reciprocating feeding mechanism with a single reciprocating member, they do not teach the use of the clip applier in the attachment of hernia mesh, nor do they teach the individual driving or feeding of each clip by a moving member.

U.S. Pat. No. 3,740,994 to DeCarlo Jr. describes a novel reciprocating feeding mechanism that may index a plurality of staples or clips, and may ready them for discharge by reciprocating one of a pair of opposing leaf spring assemblies. The staples reside serially within a guide rail with a fixed leaf spring assembly extending into the plane of the guide rail. A reciprocating leaf spring assembly may opposedly extend inwardly towards the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Pat. No. 7,485,124, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the at least one surgical fasteners has a proximal end and a distal end. The device also has an actuator having at least two sequential positions. A first position for moving the moving member distally and piercing tissue, and a second position for moving the moving member proximally, thereby deploying the distal end of the fastener.

Tacks for fixing meshes used laparoscopically have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, an absorbable tack with minimum profile that can be applied laparoscopically is needed.

Commonly assigned U.S. Pat. No. 8,920,439, the disclosure of which is hereby incorporated by reference herein, discloses an applicator instrument for dispensing surgical fasteners having an elongated shaft with a proximal shaft section and a distal shaft section. The applicator instrument has an articulation controller coupled with the distal shaft section for selectively changing the angle between the distal shaft section and the proximal shaft section. The articulation controller has at least one flexible linkage extending through the shaft and has a proximal end connected with an actuator and a distal end connected with the distal shaft section. The actuator is mounted on a housing for sliding between proximal and distal ends of the housing for moving the at least one flexible linkage in proximal and distal directions. Surgical fasteners are disposed within elongated shaft for being dispensed one at a time from the distal end of the elongated shaft.

In spite of the above advances, intra-operative conditions during laparoscopic surgery remain challenging for the surgeon. There remains a need for applicator instruments for dispensing surgical fasteners that have improved ergonomics, that enable ipsilateral (same side) mesh tensioning, and that provide maneuverability both inside and outside of a body cavity. There also remains a need for applicator instruments for dispensing surgical fasteners that have an optimized distal shaft strength when the shaft is articulated, and that provide pre-defined articulation angles for simplifying the device complexity and the user experience.

SUMMARY OF THE INVENTION

In one embodiment, an applicator instrument for dispensing surgical fasteners includes a handle having a distal end, and an articulating shaft extending from the distal end of the handle, the articulating shaft including a proximal shaft section having a longitudinal axis, a distal shaft section, and an articulating joint interconnecting the proximal and distal shaft sections. In one embodiment, the proximal shaft section has a proximal outer tube and a proximal inner member disposed inside the proximal outer tube. In one embodiment, the proximal inner member is rigidly secured to the distal end of the handle and the proximal outer tube is adapted to slide along the longitudinal axis in distal and proximal directions relative to the proximal inner member.

In one embodiment, the distal shaft section includes a distal outer tube and a distal inner member disposed inside the distal outer tube. In one embodiment, the distal outer tube is adapted to slide distally and proximally relative to the distal inner member. In one embodiment, the distal inner member has a distal end face having a surgical fastener dispensing window.

In one embodiment, the articulating joint includes a first pivot connection between a distal end of the proximal outer tube and a proximal end of the distal outer tube, and a joining member including a second pivot connection with the proximal inner member and a third pivot connection with the distal outer tube.

In one embodiment, an articulation control element is coupled with the proximal outer tube for moving the proximal outer tube along the longitudinal axis in the distal and proximal directions, whereby distal movement of the proximal outer tube results in articulation of the distal shaft section relative to the proximal shaft section via the articulating joint.

In one embodiment, the applicator instrument includes an incompressible member interconnecting the proximal inner member and the distal inner member for maintaining a fixed distance between the distal end face of the distal inner member and the distal end of the handle. In one embodiment, as the articulating distal shaft section moves between a straight configuration and an articulated configuration the distance between a distal-most end of the distal outer tube and the distal end of the handle changes while the incompressible member maintains the fixed distance between the distal end face of the distal inner member and the distal end of the handle.

In one embodiment, the applicator instrument has a firing system disposed in the handle, which includes a firing rod that extends through the articulating shaft and moves in distal and proximal directions during a firing cycle. In one embodiment, an actuator, such as a trigger, is coupled with the handle for activating the firing system. In one embodiment, the position of the firing system is controlled with features or components within the handle end of the device.

In one embodiment, the incompressible member and the firing rod are flexible for bending when the distal shaft section is articulated relative to the proximal shaft section. In one embodiment, the incompressible member and the firing rod are straight when the articulating shaft is in a straight configuration and are curved when the articulating shaft is in the articulated configuration.

In one embodiment, the applicator instrument includes a firing rod support located between the firing rod and the first pivot connection. The firing rod support has a surface for supporting an outer curved surface of the firing rod when the distal shaft section is articulated relative to the proximal shaft section. In one embodiment, the incompressible member is located between the firing rod and the support surface of the firing rod support. In another embodiment, the incompressible member is the firing rod support.

In one embodiment, a plurality of surgical fasteners are disposed in the articulating shaft, whereby a leading one of the surgical fasteners is dispensed during each firing cycle. In one embodiment, only one of the surgical fasteners in the articulating shaft is disposed in the distal shaft section at any one time, while the remaining surgical fasteners are located in the proximal shaft section.

In one embodiment, the articulation control element is moveable in a first direction for increasing the articulation angle between the distal shaft section and the proximal shaft section, and is moveable in a second, opposite direction for decreasing the articulation angle between the distal shaft section and the proximal shaft section.

In one embodiment, an applicator instrument for dispensing surgical fasteners includes a handle, and an articulating shaft extending from a distal end of the handle, the articulating shaft including a proximal shaft section extending along a longitudinal axis, a distal shaft section, and an articulating joint interconnecting the proximal and distal shaft sections. The proximal shaft section includes a proximal outer tube that is adapted to slide in distal and proximal directions along the longitudinal axis and a proximal inner member disposed inside the proximal outer tube that is rigidly secured to the distal end of the handle. In one embodiment, the distal shaft section includes a distal outer tube and a distal inner member disposed inside the distal outer tube, whereby the distal outer tube is adapted to slide distally and proximally relative to the distal inner member, and whereby the distal inner member has a distal end face having a surgical fastener dispensing window. In one embodiment, the articulating joint has a first pivot connection between a distal end of the proximal outer tube and a proximal end of the distal outer tube, and a joining member includes a second pivot connection with the proximal inner member and a third pivot connection with the distal outer tube. In one embodiment, an articulation control element is coupled with the articulating shaft for changing the articulation angle of the distal shaft section relative to the proximal shaft section. In one embodiment, an incompressible member interconnects the proximal inner member and the distal inner member for maintaining a fixed distance between the distal end face of the distal inner member and the distal end of the handle as the articulating shaft moves between a straight configuration and an articulated configuration.

In one embodiment, the distance between a distal-most end of the distal outer tube and the distal end of the handle changes as the articulating shaft moves between the straight configuration and the articulated configuration, and the incompressible member maintains the fixed distance between the distal end face of the distal inner member and the distal end of the handle as the articulating shaft moves between the straight configuration and the articulated configuration.

In one embodiment, an applicator instrument for dispensing surgical fasteners includes a handle, an articulating shaft extending from a distal end of the handle, the articulating shaft including a proximal shaft section extending along a longitudinal axis, a distal shaft section, and an articulating joint interconnecting the proximal and distal shaft sections, and a firing system disposed in the handle including a firing rod extending through the articulating shaft.

In one embodiment, an actuator is coupled with the handle for activating the firing system.

In one embodiment, the proximal shaft section include a proximal outer tube that is adapted to slide in distal and proximal directions along the longitudinal axis and a proximal inner member disposed inside the proximal outer tube that is rigidly secured to the distal end of the handle.

In one embodiment, the distal shaft section includes a distal outer tube and a distal inner member disposed inside the distal outer tube, whereby the distal outer tube is adapted to slide distally and proximally relative to the distal inner member, and whereby the distal inner member has a distal end face having a surgical fastener dispensing window.

In one embodiment, an articulation control element is coupled with the articulating shaft for changing the articulation angle of the distal shaft section relative to the proximal shaft section.

In one embodiment, an incompressible member interconnects the proximal inner member and the distal inner member for maintaining a fixed distance between the distal end face of the distal inner member and the distal end of the handle. In one embodiment, as the articulating shaft moves between a straight configuration and an articulated configuration the distance between a distal-most end of the distal outer tube and the distal end of the handle changes while the incompressible member maintains the fixed distance between the distal end face of the distal inner member and the distal end of the handle.

In one embodiment, a firing rod support is located between the firing rod and a first pivot connection of the articulating joint. In one embodiment, the firing rod support has a surface for supporting an outer curved surface of the firing rod when the distal shaft section is articulated relative to the proximal shaft section. In one embodiment, the incompressible member is located between the firing rod and the support surface of the firing rod support. In another embodiment, the incompressible member is the firing rod support.

In one embodiment, an articulating laparoscopic device includes a proximal elongated housing having a proximal end, a distal end, and a longitudinal axis, a handle attached to the proximal end of the proximal housing, and a distal housing pivotally connected to the proximal housing.

In one embodiment, the device includes a joining member with a proximal end that is pivotally connected to either the distal end of the proximal housing or the proximal end of the distal housing, and a distal end is slideably and pivotally connected to the housing not connected to the proximal end of the joining member.

In one embodiment, surgical fasteners are disposed within the proximal and/or distal housings.

In one embodiment, a visual indicator on the inside of the proximal housing aligns with a linear scale of markings on the proximal housing, displaying the current articulation angle.

In one embodiment, the joining member is contoured to mirror the cross section of the proximal or distal housings.

In one embodiment, the distal housing toggles between a straight configuration and a fixed angle relative to the proximal housing, preferably between 30 and 60 degrees.

In one embodiment, the distal housing is adjustable between a straight configuration and any range of angles relative to the proximal housing, preferably between 30 and 60 degrees.

In one embodiment, feeding and staging of fasteners occurs proximal of the distal housing.

In one embodiment, a distal inner member having a distal end face representing the distal end of the device is slidably engaged with the distal housing and connected to the handle through an incompressible flexible connection, ensuring a constant distance from the handle to the distal face during articulation, which is important to maintain a consistent firing stroke.

Providing an applicator instrument with a proximal shaft section, a distal shaft section, and an articulating joint forming a pivoting connection for the articulation provides multiple benefits. First, the strength of the articulation is supported by the proximal and distal shaft sections, which have a maximum diameter for ensuring the greatest column strength. Second, using the proximal and distal shaft sections as articulation members allows for a maximized internal passage for containing all of the other mechanism components. Third, a contoured joining member serves as a shield to encase a flexible drive mechanism that spans the inside corner of the articulation joint. Fourth, utilizing the shaft sections for this additional purpose reduces the number of parts required to achieve articulation. Fifth, providing an applicator instrument that can toggle between pre-defined articulation angles greatly simplifies the device complexity and the user experience.

In one embodiment, the articulation mechanism results in a lengthening of the central axis that extends from the distal end of the handle to the distal end of the housing. Incorporating a slidable distal member, the distance to the distal end of that member is fixed, which ensures that a driving member of a fixed stroke will extend by a constant distance from the distal end of the slidable member, regardless of the articulation angle.

In one embodiment, the present invention discloses an applicator instrument and methods for consistently deploying surgical fasteners. In one embodiment, the applicator instrument is used to hold a prosthetic device such as surgical mesh in place over tissue. In one embodiment, the applicator instrument includes a mechanism for positioning a surgical fastener in line with a firing rod. The applicator instrument includes a firing system that initially advances the firing rod toward the surgical fastener at a first speed. In one embodiment, energy may be stored in the firing system as the firing rod is advanced or piloted toward the surgical fastener. The firing system desirably engages the surgical fastener with the firing rod while maintaining the surgical fastener in a stationary position. The firing system preferably releases the stored energy to advance the firing rod at a second speed that is greater than the first speed to deploy the surgical fastener into tissue. In one embodiment, one surgical fastener is dispensed during one cycle of the firing system. A plurality of surgical fasteners may be dispensed for securing a prosthesis such as a surgical mesh to tissue.

In one embodiment, an applicator instrument for dispensing surgical fasteners preferably includes a housing, and an elongated, articulating shaft extending from the housing having a proximal end coupled with the housing and a distal end remote therefrom. The applicator instrument desirably includes a firing system for dispensing surgical fasteners from the distal end of the articulating shaft. The firing system preferably includes a firing rod disposed in the elongated shaft, and desirably has a firing cycle with a first stage for advancing the firing rod toward the distal end of the elongated shaft at a first rate of speed and a second stage for advancing the firing rod toward the distal end of the elongated shaft at a second rate of speed that is greater than the first rate of speed.

In one embodiment, a distal end of the firing rod includes an insertion fork. The applicator instrument is adapted to slowly pilot the insertion fork into a lead surgical fastener followed by quick firing of the surgical fastener through a prosthetic device and into tissue. Prior art devices rapidly advance a pushing element in one motion through a fastener in a hammer-like manner while continuing to drive the fastener into tissue, or slowly engage a fastener at the same rate for slowly driving the fastener into tissue. The first type of prior art device is limited in its ability to engage the fastener in a secure manner to assure the fastener's proper insertion into tissue. The first "hammer-like" prior art device may also damage the surgical fastener due to impact force or may require the use of a massive fastener adapted to withstand impact forces. The second type of prior art device does not advance the fastener fast enough to avoid tissue tenting and to enable proper tissue penetration. Both of these prior art approaches do not lend themselves to consistent and repeatable fastener penetration into tissue. In one embodiment, the present invention solves these limitations by slowly piloting an insertion fork into a lead surgical fastener, which assures proper engagement of the insertion fork with the surgical fastener. After proper engagement, the present invention also provides for quick firing of the surgical fastener through a prosthetic device and into tissue. As a result, each surgical fastener is inserted the same way regardless of the speed of a user's trigger squeeze.

In one embodiment, the distal end of the firing rod is coupled with at least one of the surgical fasteners during the first stage of the firing cycle, and the distal end of the firing rod dispenses the at least one of the surgical fasteners from the distal end of the shaft during the second stage of the firing cycle. The firing system may include an energy storing element such as a firing spring coupled with the firing rod, whereby the firing system is adapted to store energy in the firing spring before the second stage of the firing cycle and transfer the stored energy from the firing spring to the firing rod during the second stage of the firing cycle. In certain embodiments, the energy storing element may also include a pneumatic device, a hydraulic device and/or a compressed gas device.

In one embodiment, the applicator instrument includes an actuator movable between a first position and a second position for activating the firing system. The actuator may be a squeezable trigger that activates the firing system. In one embodiment, the firing spring is at least partially compressed prior to the first stage of the firing cycle, and the firing rod advances distally at a rate that is proportional to movement of the actuator during the first stage of the firing cycle. The firing spring is preferably compressible for storing energy therein as the actuator moves from the first position to the second position. The energy stored in the firing spring is released during the second stage of the firing cycle for rapidly driving the firing rod toward the distal end of the elongated shaft. Although many of the embodiments disclosed herein refer to a "firing spring", it is contemplated that other energy storing devices, such as those disclosed above may be used and still fall within the scope of the present invention.

In one embodiment, the firing system includes a release latch that constrains the firing rod from moving toward the distal end of the elongated shaft after the first stage of the firing cycle and before the second stage of the firing cycle. At a preferred stage of the firing cycle, and preferably after energy is stored in the firing system, the release latch desirably releases the firing rod for moving distally.

In one embodiment, the applicator instrument includes an advancer coupled with the actuator and extending through the shaft for advancing the surgical fasteners toward the distal end of the shaft. The advancer is adapted to move toward the distal end of the elongated shaft as the actuator moves from the first position to the second position. In one embodiment, the advancer is adapted to move toward the proximal end of the shaft as the actuator moves from the second position to the first position. In one embodiment, the advancer includes a plurality of advancer tabs projecting toward a distal end of the advancer, whereby each advancer tab is adapted to engage one of the surgical fasteners for urging the surgical fasteners toward the distal end of the shaft.

In one embodiment, the surgical fasteners are disposed within the shaft for being urged toward the distal end of the shaft by the advancer. In one embodiment, a most distal one of the surgical fasteners is engageable by the staging assembly for aligning the most distal one of the surgical fasteners with the distal end of the firing rod. In one embodiment, the distal end of the firing rod includes an insertion fork having spaced tines that are adapted to engage the most distal one of the surgical fasteners.

In one embodiment, a surgical fastener includes a first leg having a distal end with a first insertion tip, a proximal end, and a first insertion tool seating surface located adjacent the first insertion tip. In one embodiment, the surgical fastener includes a second leg having a distal end with a second insertion tip, a proximal end, and a second insertion tool seating surface located adjacent the second insertion tip. The surgical fastener also includes a bridge connecting the proximal ends of the first and second legs for forming a closed proximal end of the surgical fastener. In one embodiment, tines of an insertion fork are seated against the first and second insertion tool seating surfaces of the surgical fastener for applying an insertion force upon the surgical fastener at a location that is closer to the distal end of the surgical fastener than the proximal end of the surgical fastener.

In one embodiment, an applicator instrument may include a lockout system coupled with the firing system for preventing operation of the firing system after all of the surgical fasteners have been dispensed. In one embodiment, the lockout system locks an actuator or trigger in a closed position after all of the surgical fasteners have been dispensed.

In one embodiment, a method of repairing a hernia defect includes examining a patient to identify the location of a hernia defect, inserting a first trocar into the patient to access the patient's abdominal cavity adjacent the hernia defect, inserting a laparoscopic camera through the first trocar for assessing the hernia defect and an abdominal wall of the patient, inserting a rolled mesh through the first trocar and into the patient's abdominal cavity, and unrolling the mesh and placing the unrolled mesh over the hernia defect.

In one embodiment, the method includes inserting a second trocar into the patient that is caudal to the first trocar to access the patient's abdominal cavity, and providing an applicator instrument for dispensing surgical fasteners, the applicator instrument including a handle, an articulating shaft extending from a distal end of the handle, the articulating shaft including a proximal shaft section extending along a longitudinal axis, a distal shaft section, an articulating joint interconnecting the proximal and distal shaft sections, and an articulation control element coupled with the articulating shaft for changing the articulation angle of the distal shaft section relative to the proximal shaft section. In one embodiment, at least one surgical fastener is disposed in the articulating shaft;

In one embodiment, with the articulating shaft in a straight configuration so that the proximal and distal shaft sections extend along the longitudinal axis, a distal most end of the articulating shaft is inserted through the second trocar and into the patient's abdominal cavity. The articulation control element is engaged for articulating the distal shaft section relative to the proximal shaft section so that the distal shaft section extends along a second axis that defines an angle with the longitudinal axis. The distal most end of the articulating shaft is abutted against the mesh and the trigger is squeezed for dispensing at least one surgical fastener through the mesh and into the patient's abdominal wall.

These and other preferred embodiments of the present invention will be described in more detail below.

BRIEF DESCRIPTION OF THE DRAWING

FIG. 8A shows an exploded view of the articulating shaft of FIG. 1 including proximal and distal outer tubes, a joining member, proximal and distal inner members interconnected by an incompressible connection, a firing rod, an insertion fork, a firing rod support, and a firing support member, in accordance with one embodiment of the present invention.

FIG. 8B shows a cross-sectional view of the elements of FIG. 8A assembled together to form an articulating shaft of an applicator instrument, in accordance with one embodiment of the present invention.

DETAILED DESCRIPTION

Figure 1:
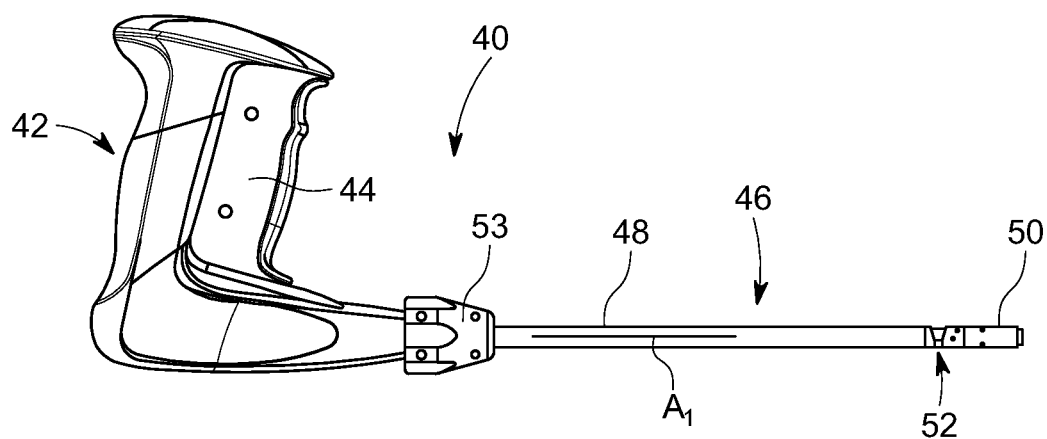
FIG. 1 shows an applicator instrument for dispensing surgical fasteners including a handle, an articulating shaft having a proximal shaft section and a distal shaft section, and an articulation control knob for controlling the articulation angle of a distal shaft section relative to the proximal shaft section, in accordance with one embodiment of the invention.

Referring to FIG. 1, in one embodiment, an applicator instrument 40 for dispensing surgical fasteners includes a handle 42 having a trigger 44, and an articulating shaft 46 with a proximal shaft section 48 and a distal shaft section 50 that articulates relative to the proximal shaft section. The distal shaft section 50 is moveable between a first position in which it extends along a longitudinal axis $A_1$ of the proximal shaft section 48 and an articulated configuration in which it is positioned at different angles relative to the longitudinal axis $A_1$ of the proximal shaft section 48. In one embodiment, a distal end of the proximal shaft section 48 is pivotally connected with a proximal end of the distal shaft section 50 via an articulating joint 52, which enables the distal shaft section 50 to articulate to different angles relative to the longitudinal axis $A_1$ of the proximal shaft section 48. The applicator instrument has an articulation control knob 53 that is rotated for changing the articulation angle between the distal shaft section 50 and the proximal shaft section 48. In one embodiment, rotating the articulation control knob in a first direction increases the articulation angle and rotating the articulation control knob in an opposite, second direction reduces the articulation angle. In one embodiment, the articulation control knob 53 may be used to set the distal shaft section 50 at an infinite number of angles between about 0-60. In one embodiment, the articulation angle may be as great as 80 degrees. In FIG. 1, the articulating shaft 46 is straight so that the proximal shaft section 48 and the distal shaft section 50 both extend along the longitudinal axis $A_1$.

In one embodiment, the applicator instrument 40 is a multi-fire device that contains a plurality of surgical fasteners stored therein as disclosed in commonly assigned U.S. Pat. Nos. 8,579,920; 8,728,098; 8,728,099; 8,894,669; and 8,920,439, the disclosures of which are hereby incorporated by reference herein. In one embodiment, the applicator instrument includes a plurality of surgical fasteners stored in series along the length of the articulating shaft 46. In one embodiment, the articulating shaft 46 includes a pair of flat stampings having tabbed features incorporated therein. One of the flat stampings is stationary for preventing the surgical fasteners from moving proximally within the articulating shaft 46. The other flat stamping cycles in distal and proximal directions each time the trigger 44 is squeezed and then released to facilitate incremental advancement of the surgical fasteners along the length of the articulating shaft 46. In one embodiment, the lead fastener is staged for firing proximal of the articulation joint 52. The firing rod pilots into the lead fastener and delivers it through the articulation and out of the surgical fastener dispensing window. Alternatively, the stampings are flexible so that the stampings may curve to conform to the angle of the articulating shaft while guiding the surgical fasteners along the path defined by the articulating shaft 46. In one embodiment, a single, lead surgical fastener is dispensed each time the trigger is pulled. During each trigger pull, each of the trailing surgical fasteners are advanced distally toward the distal end of the articulating shaft.

Figure 2:
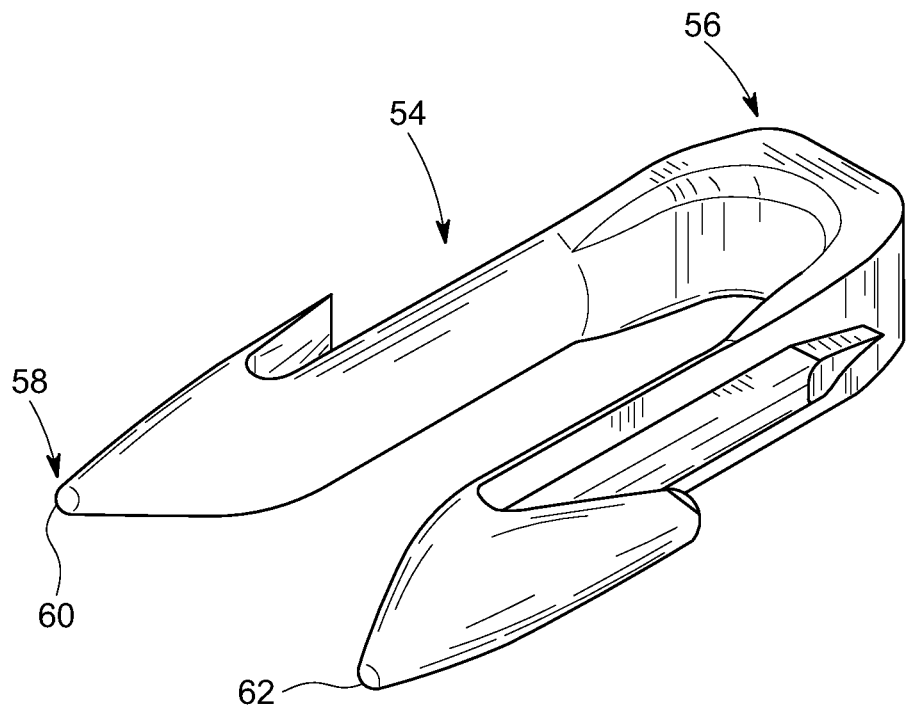
FIG. 2 shows a perspective view of a surgical fastener dispensed by the applicator instrument shown in FIG. 1, in accordance with one embodiment of the present invention.

In one embodiment, a series of surgical fasteners are pre-loaded into the articulating shaft 46 of the applicator instrument 40. Referring to FIG. 2, in one embodiment, a single surgical fastener 54 includes a proximal end 56 and a distal end 58 having insertion tips 60, 62 that are spaced from one another for capturing mesh fibers between the tapered ends. In one embodiment, the surgical fastener 54 has one or more of the features disclosed in commonly assigned U.S. Pat. Nos. 8,579,920; 8,728,098; 8,728,099; 8,894,669; and 8,920,439, the disclosures of which are hereby incorporated by reference herein.

Figure 3:
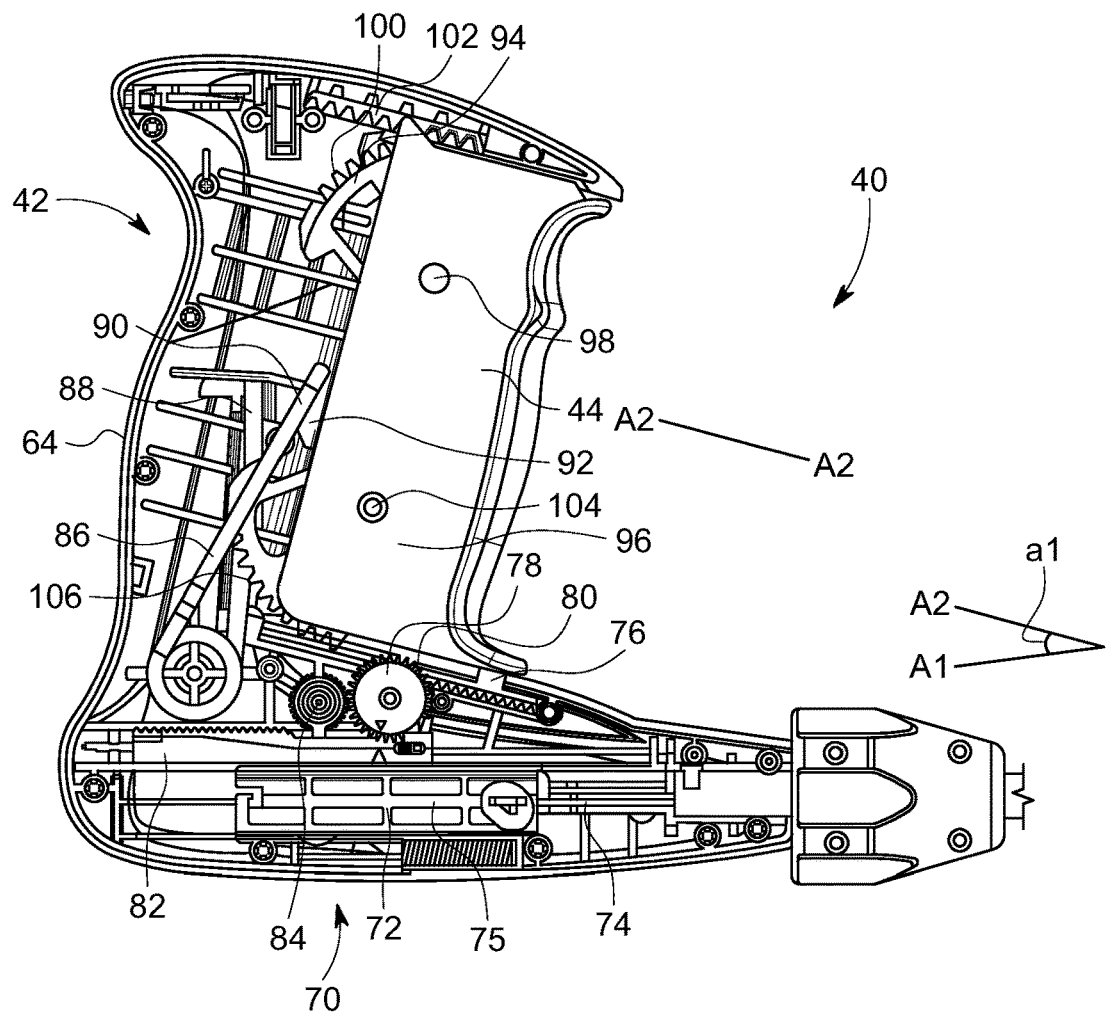
FIG. 3 shows a cross-sectional view of the handle shown in FIG. 1 and a firing system disposed inside the handle, in accordance with one embodiment of the present invention.

Referring to FIG. 3, in one embodiment, the applicator instrument 40 includes the handle 42 that contains the firing system, and a hand grip 64 projecting upwardly from a lower end of the handle. The handle 42 includes the trigger 44 that is adapted to be pulled along a linear path $A_2$-$A_2$ toward a proximal end of the applicator instrument 40. In one embodiment, the trigger 44 is adapted to move along the linear path $A_2$-$A_2$ that defines an angle $\alpha_1$ of about 10-20° and more preferably about 15° with the longitudinal axis $A_1$-$A_1$ of the proximal shaft section 48 of the articulating shaft 46 (FIG. 1).

In one embodiment, the applicator instrument 40 includes a firing system 70 having one or more features similar to those disclosed in commonly assigned U.S. Pat. Nos. 8,579,920; 8,728,098; 8,728,099; 8,894,669; and 8,920,439, the disclosures of which are hereby incorporated by reference herein. In one embodiment, the firing system includes a spring block 72, a firing rod 74, and a firing spring 75 that stores energy as the trigger 44 is squeezed. In one embodiment, the firing system 70 is coupled with the trigger 44 via a trigger rack 76 that slides proximally and distally with the trigger along the axis $A_2$-$A_2$. The trigger rack 76 is coupled with a drive gear 78 that rotates in a counter-clockwise direction when the trigger 44 is squeezed toward the proximal end of the applicator instrument 40, and rotates in a clockwise direction when the trigger 44 is released and moves distally toward the distal end of the applicator instrument. The drive gear 78 has external gear teeth 80 that mesh with teeth provided at an upper end of a sliding yoke 82. As the drive gear 78 rotates in a counter-clockwise direction, the yoke 82 slides in a distal direction along the axis $A_1$-$A_1$. As the drive gear 78 rotates in a clockwise direction, the yoke 82 slides in a proximal direction along the axis $A_1$-$A_1$. In one embodiment, the gear ratio between the drive gear 78 and the yoke 82 is about 0.9 to 1.5.

In one embodiment, the applicator instrument 40 includes a ratchet pawl 84 having a ratchet spring, as disclosed in commonly assigned U.S. Pat. Nos. 8,579,920; 8,728,098; 8,728,099; 8,894,669; and 8,920,439, the disclosures of which are hereby incorporated by reference herein. The ratchet pawl 84 ensures that the sliding yoke 82 moves to its distal-most position before it is able to change direction and move proximally back into the original position shown in FIG. 3. During the trigger release, the ratchet pawl 84 also ensures that the sliding yoke 82 moves to its proximal-most position before it is able to change direction.

In one embodiment, the applicator instrument 40 includes a trigger return spring 86 that normally urges the trigger 44 to move distally. The trigger return spring 86 includes a first arm 88 that is secured within a molded portion of the hand grip 64, and a second arm 90 that engages the trigger 44. In one embodiment, a proximal end of the trigger 44 has a tab 92 and the second arm 90 of the trigger return spring engages the back face 92 of the trigger for normally urging the trigger 44 distally. As the trigger 44 is squeezed, the trigger return spring 86 stores energy. When the trigger is released, the trigger return spring transfers the stored energy back to the trigger for moving the trigger distally.

In one embodiment, the applicator instrument 40 includes a first rotating link 94 and a second rotating link 96 coupled with the trigger 44. In one embodiment, the first rotating link 94 is disposed inside the trigger 44 and is pivotally secured to the trigger 44 via a first pivot 98. The first rotating link 94 has gear teeth 100 that mesh with a rack 102 located inside the upper end of the hand grip 64. The second rotating link 96 is pivotally secured to the trigger 44 via a second pivot 104. The second rotating link 96 has an upper end with upper gear teeth that mesh with lower gear teeth of the first rotating link 94. The first and second rotating links 94, 96 are coupled with one another via opposing gear teeth (not shown), which ensure that the first and second rotating links rotate at the same rate. The second rotating link 96 has a lower end having bottom teeth 106 that mesh with opposing teeth molded into a second rack (not shown) disposed at a lower end of the handle 42.

The configuration of the first and second rotating links 94, 96 within the handle 42, and the pivotal connection of the first and second rotating links with the trigger 44 enables the trigger 44 to move along a single linear path, namely axis $A_2$-$A_2$. The linear motion of the trigger 44 allows the force and distance required to squeeze the trigger to remain consistent no matter where the squeezing forces are concentrated along the length of the trigger, which minimizes the likelihood of binding of the trigger.

The engagement and timing of the gear features for the first and second rotating links 94, 96 enables the trigger 44 to move in a linear fashion along the axis $A_2$-$A_2$, and also prevents the trigger from rotating about a center point when squeezing forces are applied unevenly along the hand-squeezing area of the trigger. The ability of the trigger mechanism to convert linear motion of the trigger into rotary motion through the drive gear 78 minimizes friction and any risk of binding. In one embodiment, the first and second rotating links 94, 96 are made from a polymer such as a glass reinforced polycarbonate.

In one embodiment, the handle 42 contains a firing system having the firing spring, a spring block and a firing rod, as disclosed in commonly assigned U.S. Pat. Nos. 8,579,920; 8,728,098; 8,728,099; 8,894,669; and 8,920,439, the disclosures of which are hereby incorporated by reference herein. During a firing cycle, the spring block 72 and the firing rod 74 are adapted to move in distal and proximal directions along the longitudinal axis $A_1$-$A_1$.

Figure 4:
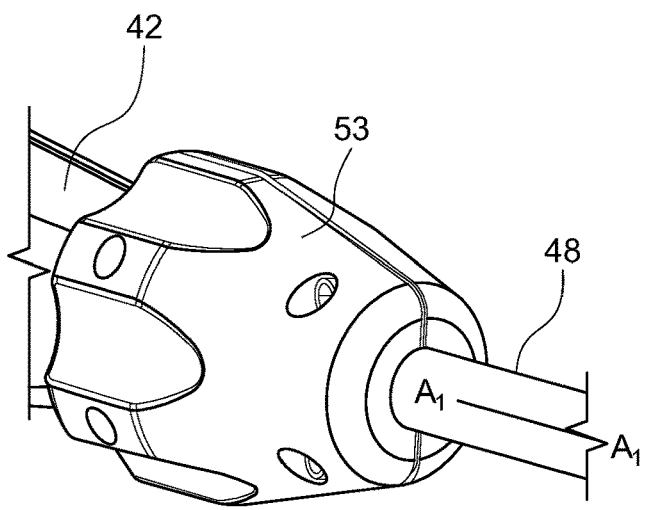
FIG. 4 shows a perspective view of the articulation control knob shown in FIG. 1.

Referring to FIGS. 1 and 4, in one embodiment, the applicator instrument 40 includes the articulation control knob 53 that is secured near a distal end of the handle 42 and that is rotated about the longitudinal axis $A_1$ of the proximal shaft section 48 of the articulating shaft 46 for changing the angle of the distal shaft section 50 relative to the proximal shaft section 48.

Figure 5:
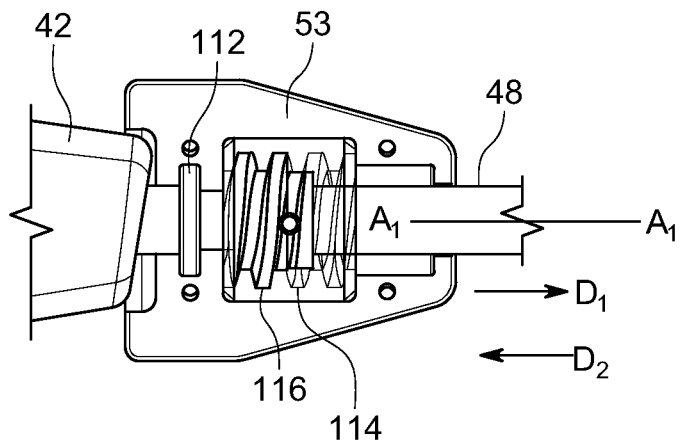
FIG. 5 shows a cross-sectional view of the articulation control knob of FIG. 1 in a first position in which the articulating shaft is straight.

Referring to FIG. 5, in one embodiment, the applicator instrument includes a flange 112 that is rigidly connected to the handle 42. The articulation control knob 53 rotates about the flange 112. The articulation control knob 53 has internal threads 114 that engage external threads 116 at the proximal end of the proximal shaft section 48. Rotation of the articulation control knob 53 in a first direction causes the external threads 116 and the proximal shaft section 48 to move distally in the direction $D_1$ along the axis $A_1$-$A_1$. Rotation of the articulation control knob 53 in an opposite, second direction causes the external threads 116 and the proximal shaft section 48 to move proximally in the direction $D_2$ along the axis $A_1$-$A_1$. The pitch of the internal threads 114 and the external threads 116 is sufficiently shallow to prevent external loads on the distal shaft section 50 from rotating the articulation control knob 53. In one embodiment, the pitch is 0.167 inches per rotation.

Figure 6A:
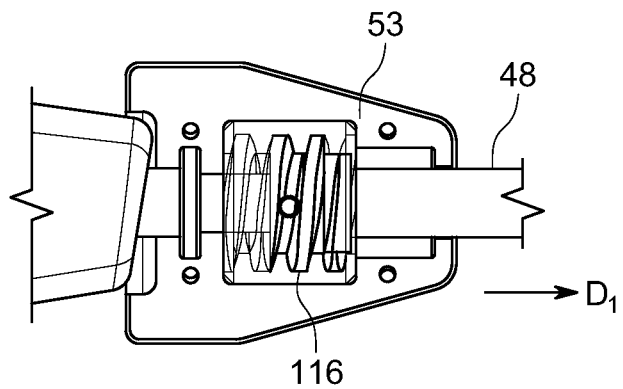
FIG. 6A shows a cross-sectional view of the articulation control knob of FIG. 1 in a second position in which the distal shaft section of the articulating shaft is articulated relative to the proximal shaft section of the articulating shaft.
Figure 6B:
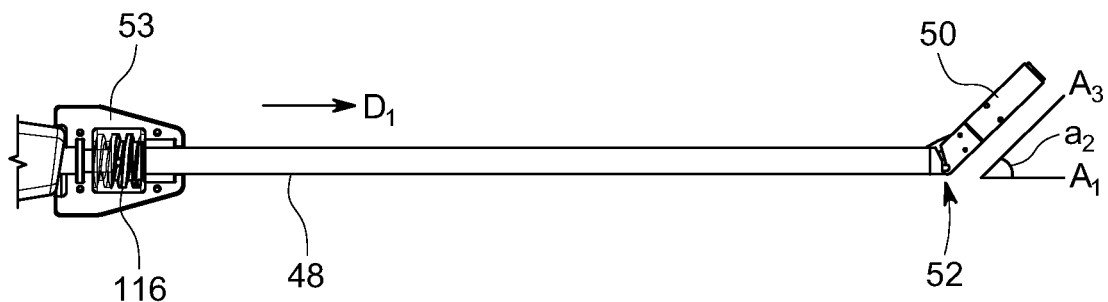
FIG. 6B shows the articulation control knob of FIG. 6A and the articulating shaft of FIG. 1.

Referring to FIGS. 6A and 6B, in one embodiment, the articulation control knob 53 is rotated for moving the external threads 116 and the proximal shaft section 48 distally in the direction $D_1$, which, in turn, pivots the distal shaft section 50 at the articulating joint 52 so that the distal shaft section 50 extends along an axis $A_3$ that defines an angle $\alpha_2$ relative to the longitudinal axis $A_1$ of the proximal shaft section 48.

Figure 7A:
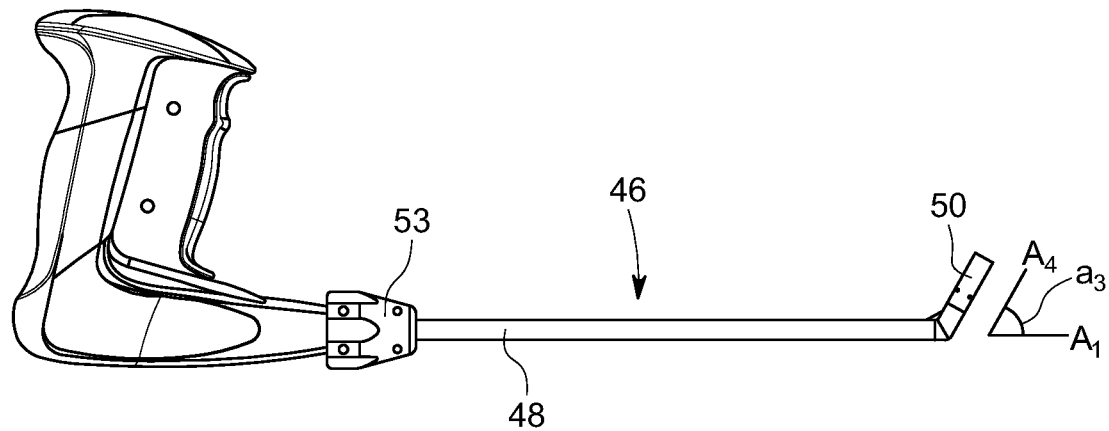
FIGS. 7A-7B show the applicator instrument of FIG. 1 with the distal shaft section articulated at an angle relative to the proximal shaft section.
Figure 7B:
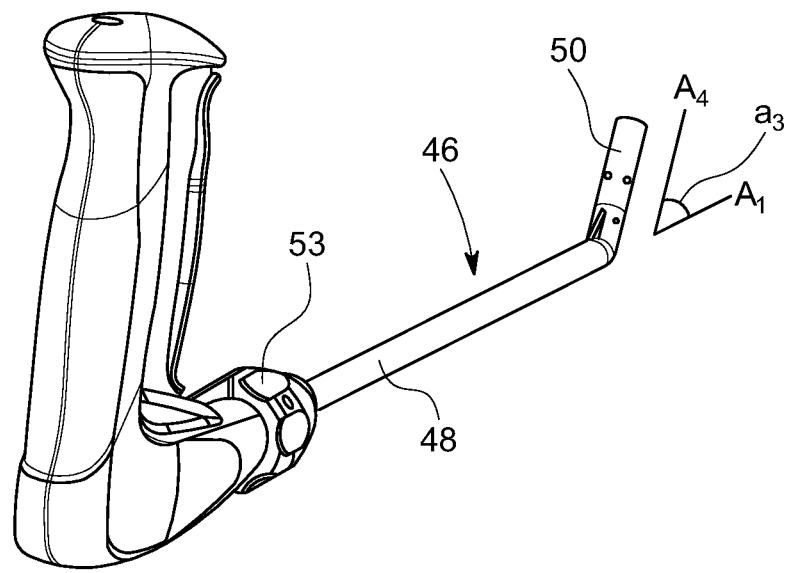

In one embodiment, the articulation control knob 53 is rotatable so that the distal shaft section 50 may be positioned at an infinite number of angles relative to the proximal shaft section 48. In FIG. 1, the articulating shaft 46 is straight so that the distal shaft section 50 extends along the axis $A_1$ of the proximal shaft section 48. In FIG. 6B, the distal shaft section extends along an axis $A_3$ that defines an angle $\alpha_2$ of about 45 degrees with the longitudinal axis $A_1$ of the proximal shaft section 48. In FIGS. 7A and 7B the distal shaft section 50 of the articulating shaft 46 extends along an axis $A_4$ and the proximal shaft section 48 extends along the axis $A_1$ that defines an angle $\alpha_3$ of about 60 degrees. In one embodiment, the distal shaft section 50 moves between 0-60 degrees relative to the longitudinal axis $A_1$ of the proximal shaft section 48. In one embodiment, the articulation control knob 53 may be used to change the articulation angle of the distal shaft section 50 to any angle between 0-80 degrees.

Referring to FIG. 8A, in one embodiment, the articulating shaft 46 (FIG. 1) includes the proximal shaft section 48 having a proximal outer tube 120 that is adapted to selectively slide in proximal and distal directions along the longitudinal axis $A_1$, and a proximal inner member 122 that also extends along the longitudinal axis $A_1$, that is disposed inside the proximal outer tube 120, and that is stationary and does not move along the axis $A_1$ during articulation of the articulating shaft 46. The proximal end of the proximal outer tube 120 has external threads 116 (FIGS. 5 and 6A-6B) that engage internal threads 114 of the actuation control knob 53 for moving the proximal outer tube 120 in proximal and distal directions along the longitudinal axis $A_1$ in response to rotation of the articulation control knob 53.

In one embodiment, the proximal outer tube 120 includes the proximal end having the external threads 116 (FIG. 6B) and a distal end 124 having an angle indicator 126 for indicating the angle of the distal shaft section 50 relative to the proximal shaft section 48. In one embodiment, the angle indicator 126 has markings indicating angles between 0-60 degrees. In one embodiment, the articulating joint 52 (FIG. 1) includes a pivot flange 128 located at the distal end 124 of the proximal outer tube 120. The pivot flange 128 has an opening 130 that receives a first pivot pin 132A. In one embodiment, the pivot flange 128 is located near a lower end of the distal end 124 of the proximal outer tube 120.

In one embodiment, the articulating shaft 46 includes the distal shaft section 50 having a distal outer tube 134 that is pivotally connected to the distal end 124 of the proximal outer tube 120, and a distal inner member 136 having a distal end face 137 where the distal inner member 136 is connected to the proximal inner member 122 via an incompressible connection 138. In one embodiment, the proximal end 140 of the distal outer tube 134 has a pivot flange 142 with an opening 144 that is adapted to receive the first pivot pin 132A. The pivot flange 142 is located near a lower end of the proximal end 140 of the distal outer tube 134. In one embodiment, the respective openings 130, 144 of the pivot flanges 128, 142 are aligned with one another and the first pivot pin 132A is passed through the aligned openings 130, 144 to pivotally connect the distal end 124 of the proximal outer tube 120 with the proximal end 140 of the distal outer tube 134. The pivot pin 132A may be connected using a variety of fastening techniques including welding, crimping, etc.

In one embodiment, the distal end of the proximal inner member 122 has a pivot flange 146 having an opening 148 adapted to receive a second pivot pin 132B. In one embodiment, the articulating shaft 46 has a joining member 152 having a proximal end 154 with a pin opening 156 and a distal end 158 with a pin opening 160. In one embodiment, the pin opening 156 at the proximal end of the joining member 152 is aligned with the opening 148 on the pivot flange 146 of the proximal inner member 122 and the second pivot pin 132B is inserted into the aligned openings 148, 156. In one embodiment, the pin opening 160 at the distal end 158 of the joining member 152 is aligned with a pin opening 150 in the distal outer tube 134 and a third pivot pin 132C is inserted into the aligned openings 150, 160. The pivot pins 132B and 132C may be connected using a variety of fastening techniques including welding, crimping, etc.

In one embodiment, the applicator instrument includes a firing system support structure 162 and a firing system having one or more elements of the firing system disclosed in commonly assigned U.S. Pat. Nos. 8,579,920; 8,728,098; 8,728,099; 8,894,669; and 8,920,439, the disclosures of which are hereby incorporated by reference herein. In one embodiment, the applicator instrument has a plurality of surgical fasteners pre-loaded into the articulating shaft 46. In one embodiment, each time the trigger 44 (FIG. 1) is squeezed, a lead surgical fastener 54 is dispensed from a distal end of the distal inner member 136, and the trailing fasteners are advanced distally by the elements of the firing system, some of which may be disposed within the firing system support structure 162.

In one embodiment, the applicator instrument includes a firing rod support 164 that is located near the articulation joint 52 (FIG. 1). In one embodiment, the firing support rod 164 is pivotally attached to either the proximal inner member 122 or the distal inner member 136. The unattached end is allowed to slide freely in the other inner member. The firing rod support 164 has a top surface 166 that functions as a floor for the firing rod 74 so that the firing rod does not kink or buckle when the distal shaft section 50 is articulated relative to the proximal shaft section 48. In one embodiment, the firing rod support 164 may function as a floor support for both the incompressible member 138 and the firing rod 74 to prevent kinking or buckling of the firing rod during articulation and to ensure that sufficient firing force may be transmitted through the firing rod to a lead surgical fastener. The distal end of the firing rod 74 includes an insertion fork 75 as disclosed in commonly assigned U.S. Pat. Nos. 8,579,920; 8,728,098; 8,728,099; 8,894,669; and 8,920,439, the disclosures of which are hereby incorporated by reference herein. The insertion fork is adapted to engage a lead surgical fastener 54 for advancing the surgical fastener beyond the distal face 137 of the distal inner member 136 and into tissue for securing a prosthetic device (e.g., a surgical mesh) to tissue.

Referring to FIGS. 8A and 8B, in one embodiment, the articulating shaft 46 is assembled by disposing the firing rod 74 and the insertion fork 75 inside the firing system support structure 162 so that the firing rod 74 overlies the top surface 166 of the firing rod support 164. In turn, the firing system support structure 162, the firing rod support 164, the firing rod 74, and the insertion fork 75 are disposed inside the proximal inner member 122 and the distal inner member 136, which are connected together by the incompressible member 138. As will be described in more detail herein, the incompressible member 138 maintains a constant travel path distance for the surgical fasteners 54, extending between the distal end face 137 of the distal inner member 136 and the proximal end of the proximal inner member 122 secured to the handle. The firing rod 74 and the insertion fork 75 are adapted to move distally and proximally through longitudinally extending openings formed in the proximal and distal inner members 122, 136.

In one embodiment, a subassembly including the proximal and distal inner members 122, 136 is disposed inside the respective proximal outer tube 120 and the distal outer tube 134. The proximal inner member 122 is disposed inside the proximal outer tube 120, and the distal inner member 136 is disposed inside the distal outer tube 134. In one embodiment, the proximal inner member 122 is stationary and the proximal outer tube 120 is adapted to slide in distal and proximal directions relative to the proximal inner member 122. In one embodiment, as the shaft 46 is articulated, the distal inner member 136 is prevented from moving in distal or proximal directions by the incompressible member 138 and the distal outer tube 134 is adapted to slide over the distal inner member 136. The articulating joint 52 includes a first pivot connection 168 which is formed between the distal end 124 of the proximal outer tube 120 and the proximal end 140 of the distal outer tube 134 by passing the first pivot pin 132A through aligned openings 130, 144. Second and third pivot connections are formed with the distal end of the proximal inner member 122 and the distal outer tube 134 using the joining member 152 and the second and third pivot pins 132B, 132C.

In one embodiment, the proximal inner member 122 is stationary and does not move distally or proximally relative to the handle 42 (FIG. 1) as the articulating shaft 46 moves between the straight configuration shown in FIG. 8B and the articulated configurations shown in FIGS. 6B and 7A-7B. The proximal end of the proximal inner member 122 is rigidly secured to the handle 42 so that it is stationary and does not move distally and proximally relative to the handle. The incompressible member 138 is flexible so that it bends during articulation of the articulating shaft 46, however, the incompressible member 138 maintains a constant distance between the distal end face 137 of the distal inner member 136 and the proximal end of the proximal inner member 122, regardless of whether the articulating shaft is straight or angled. Moreover, the distal inner member 136 slides proximally and distally within the distal outer tube 134 as the articulating shaft 46 moves between the straight and articulated configurations.

Figure 9A:
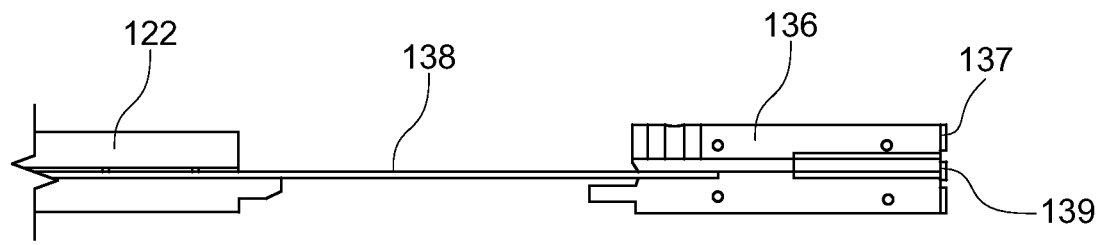
FIG. 9A shows the proximal and distal inner members connected with the incompressible member of FIG. 8A in a straight configuration.
Figure 9B:
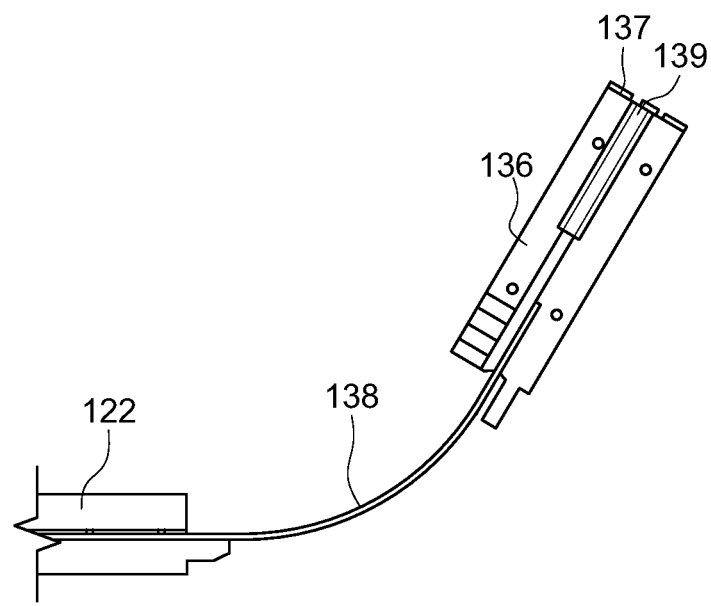
FIG. 9B shows the proximal and distal inner members and the incompressible member of FIG. 8A in an articulated configuration.

Referring to FIGS. 9A and 9B, in one embodiment, the proximal inner member 136 has the distal end face 137 with a window 139 for dispensing surgical fasteners from the distal end of the articulating shaft 46 (FIG. 1). The proximal inner member 122 and the distal inner member 136 of the articulating shaft 46 (FIGS. 8A and 8B) are connected to one another by the incompressible member 138. The proximal end of the proximal inner member 122 is secured to the handle 42 (FIG. 1) so that it is stationary and does not move in distal or proximal directions as the articulating shaft is articulated between a straight and angled configuration. The incompressible member 138 ensures that the distance between the distal end face 137 of the distal inner member 136 and the proximal end of the proximal inner member 122 does not change as the distal inner member 136 moves from the straight configuration shown in FIG. 9A to the articulated configuration shown in FIG. 9B.

Figure 10A:
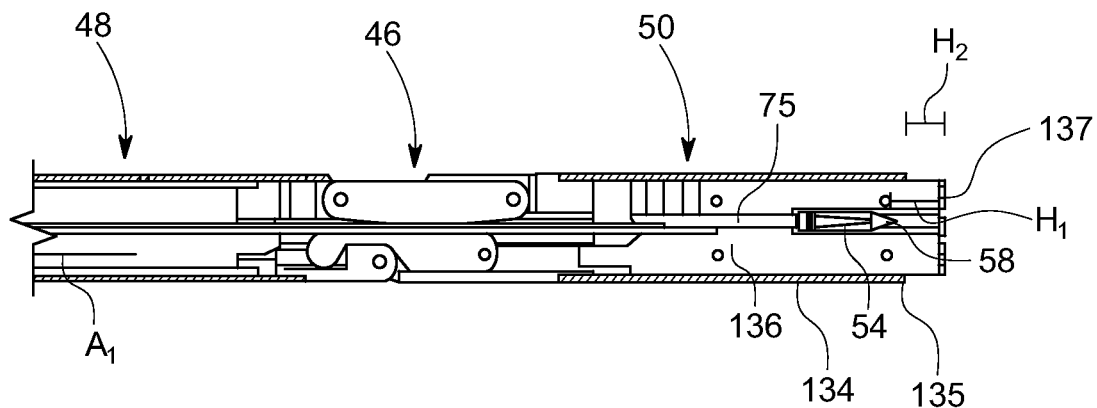
FIG. 10A shows a cross-sectional view of the articulating shaft of FIG. 1 in a straight configuration.

Referring to FIG. 10A, in one embodiment, when the articulating shaft 46 is straight and the firing system is ready to fire the lead surgical fastener 54 from the distal end of the articulating shaft 46, the firing rod 74 and the insertion fork 75 are positioned to that the points at the leading end 58 of the surgical fastener 54 define a distance $H_1$ from the distal end face 137 of the distal inner member 136, and the distal end 135 of the distal outer tube 134 and the distal end face 137 of the distal inner member 136 define a second distance $H_2$ that is positive. As a result, the distal end 137 of the distal inner member 136 is distal to the distal end 135 of the distal outer tube 134.

Referring to FIG. 10A, in one embodiment, the articulating shaft 46 is in a straight configuration so that the proximal shaft section 48 and the distal shaft section 50 extend along the axis $A_1$ and the angle between the distal shaft section and the proximal shaft section is 0 degrees. The distal end face 137 of the distal inner member 136 extends distally beyond the distal-most edge 135 of the distal outer tube 134 by a distance designated $H_1$. The firing system of the applicator instrument positions the distal end 58 of the surgical fastener 54 a distance $H_2$ from the distal end face 137 of the distal inner member 136. In one embodiment, the articulation control knob 53 (FIG. 1) is rotatable about the proximal outer tube 120 for articulating the distal shaft section 50 relative to the proximal shaft section 48. In one embodiment, rotating the articulation control knob slides the proximal outer tube 120 in the distal direction $D_1$ while the proximal inner member 122 remains stationary. Due to the articulating joint 52 between the proximal and distal outer tubes 120, 134 and the joining member 152 connecting the distal end of the proximal inner member 122 and the proximal end of the distal outer tube 134, distal sliding movement of the proximal outer tube 120 in the direction $D_1$ changes the angle of the distal outer tube 134 relative to the proximal outer tube 122.

Figure 10B:
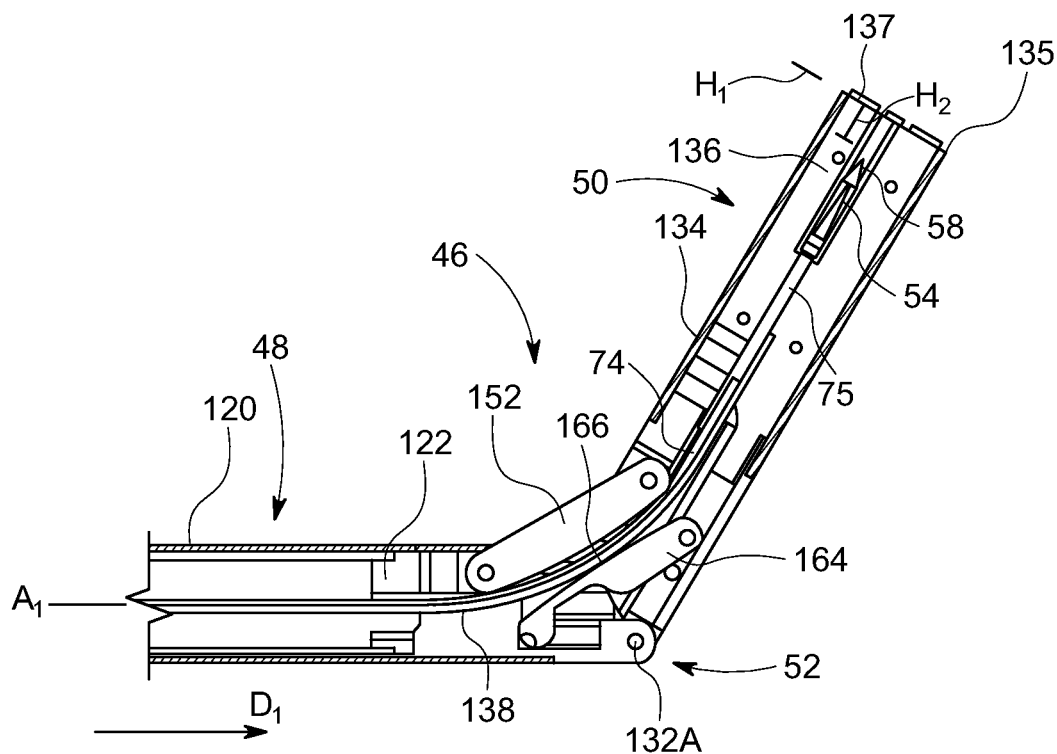
FIG. 10B shows a cross-sectional view of the articulating shaft of FIG. 10A with the distal shaft section articulated relative to the proximal shaft section.

In the articulated position shown in FIG. 10B, the distance $H_1$ between the distal end face 137 and the distal-most edge 135 of the distal outer tube 134 has been reduced due to the sliding motion of the distal outer tube. However, the distance $H_2$ between the distal end 58 of the surgical fastener 54 and the distal end face 137 of the distal inner member 136 remains unchanged from the straight configuration shown in FIG. 10A. This is due, in part, to the incompressible member 138 that maintains a constant distance between the distal end face 137 and the handle as the articulating shaft moves from a straight configuration to an articulated configuration. In one embodiment, the incompressible member 138 and the firing rod 74 are adjacent each other insuring they behave similarly through the articulated joint.

Thus, the distance $H_1$ between the distal end face 137 and the distal-most edge 135 changes during articulation, while the distance $H_2$ between the distal face 137 and the leading end 58 of the surgical fastener 54 remains unchanged. During a firing cycle, the trigger is squeezed so that the first system advances the insertion fork 75 a set distance beyond the distal end face 137 of the distal inner member 136 for dispensing a lead surgical fastener 54 from the distal end of the articulating shaft 46. Although not indicated, the distance between the insertion fork 75 and the distal end face 137 of the distal inner member 136 also remains constant as the articulating shaft 46 moves from the straight configuration shown in FIG. 10A and the fully articulated position shown in FIG. 100, which ensures a consistent firing of a surgical fastener from the distal end of the distal inner member 136 regardless of whether the articulating shaft is straight, fully articulated, or at some angle between straight and fully articulated.

Referring to FIG. 10B, in one embodiment, movement of the proximal outer tube 120 in the distal direction $D_1$ results in articulation of the distal shaft section 50 due to the translation of the proximal outer tube 120 and the articulation joint 52 connecting the proximal and distal outer tubes 120, 134. Because the distal outer tube 134 has the joining member 152 connecting it with the proximal inner member 122, the displacement of the first pivot pin 132A applies a moment to the distal shaft section 50. The moment causes the distal shaft section 50 to change angles. In one embodiment, it is important to maintain a fixed distance between the distal end face 137 of the distal inner member 136 and the handle 42 (FIG. 1) that contains the firing system used to deploy the surgical fasteners. Using the flexible, but incompressible member 138 between the distal inner member 136 and the stationary proximal inner member 122 assures a non-changing distance as the articulating shaft moves from the straight configuration shown in FIG. 10A to the fully articulated position shown in FIG. 10B.

Figure 11A:
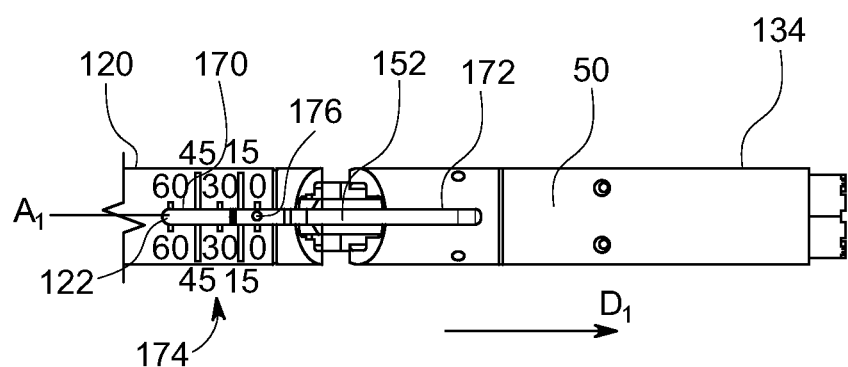
FIGS. 11A and 11B show top plan and side elevation views of the articulating shaft shown in FIG. 1.
Figure 11B:
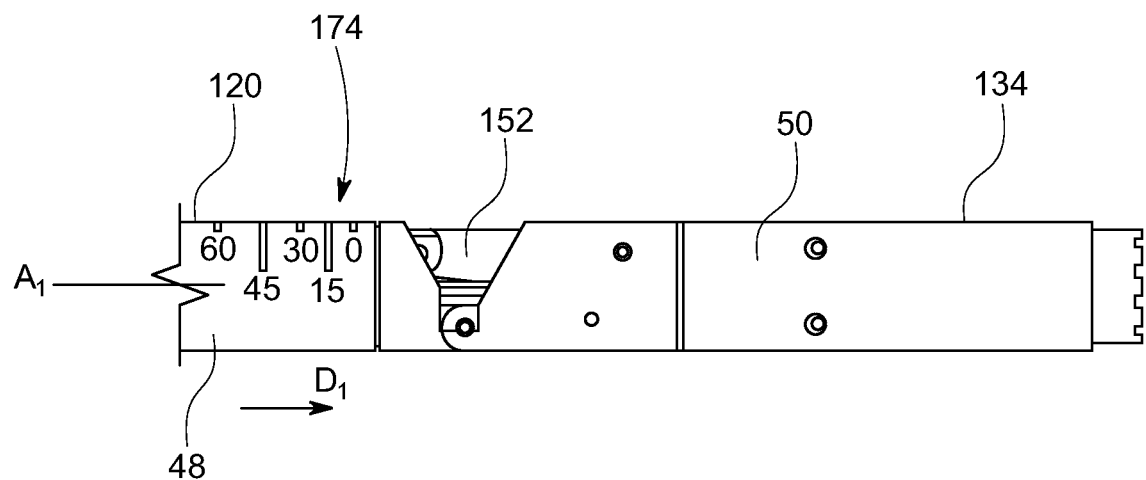
Figure 12A:
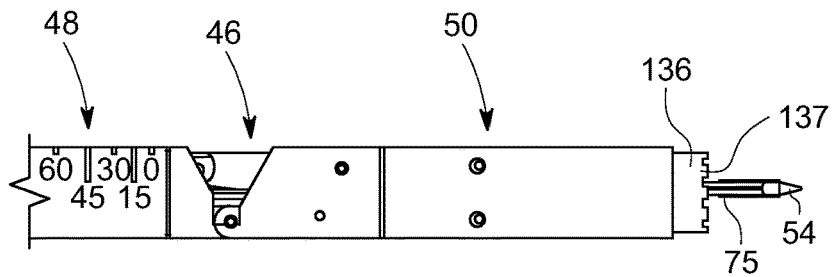
FIGS. 12A-12D show the articulating shaft of FIGS. 11A and 11B when dispensing a surgical fastener from a distal end of the articulating shaft, in accordance with one embodiment of the present invention.
Figure 12B:
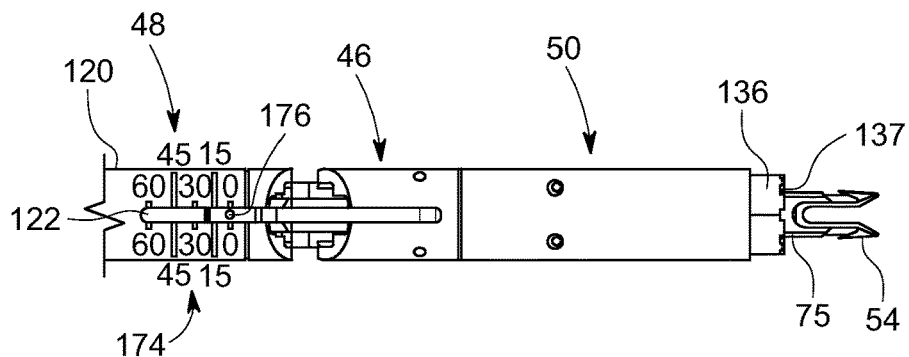
Figure 12C:
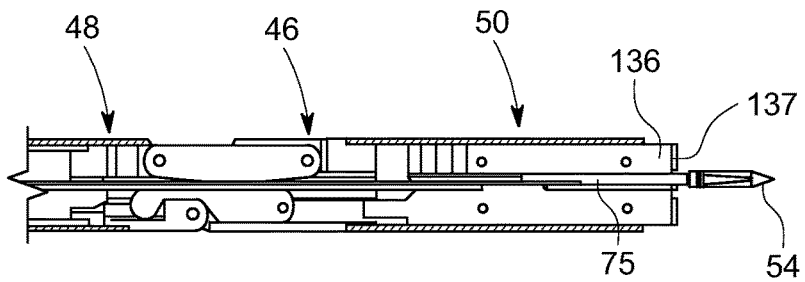
Figure 12D:
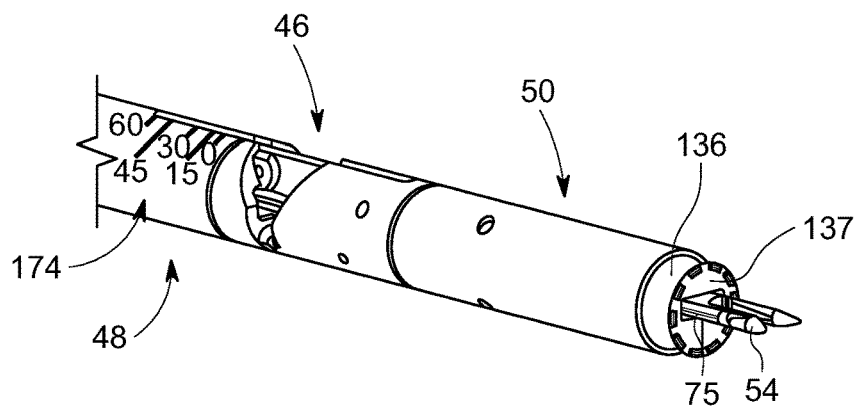

Referring to FIGS. 11A and 11B, in one embodiment, the top sides of the proximal and distal outer tubes 120, 134 have aligned slots 170, 172 that accommodate the joining member 152. In one embodiment, the body of the joining member 152 passes through the slots 170, 172 when the distal shaft section 50 is articulated relative to the proximal shaft section 48. The top surface of the proximal outer tube 120 has indicia 174 provided thereon that indicate the angle of the distal shaft section 50 relative to the proximal shaft section 48. In one embodiment, the indicia 174 are numbers indicating angles 0, 15, 30, 45, and 60 degrees. The distal end of the proximal inner member 122 has a marker 176 provided on a top surface thereof that is visible through the slot 170. As the distal shaft section 50 is articulated relative to the proximal shaft section 48, the proximal outer tube 120 slides distally in the direction $D_1$ along the longitudinal axis $A_1$, while the proximal inner member 122 and the marker 176 remains stationary. As a result, the proximal outer tube 120 moves relative to the marker 176 on the proximal inner member 122, which indicates the angle of the distal shaft section 50 relative to the proximal shaft section 48. Having the indicia near the articulation joint allows for good visibility of the indicia intra-operatively during laparoscopic surgery. Due to the short distal shaft section 50 of the instrument, the articulation joint 52 will typically remain mostly in the field of view of the laparoscopic camera.

FIGS. 12A-12D show the articulating shaft 46 during a firing cycle for dispensing a lead surgical fastener 54 from a distal end face 137 of the distal inner member 136. The insertion fork 75 extends beyond the distal end face 137 of the distal inner member 136 for inserting the surgical fastener into tissue. The angle marker 176 (FIG. 12B) on the proximal inner member 122 is aligned with the 0 degree indicia 174 on the proximal outer tube 120 to indicate that the proximal and distal shaft sections 48, 50 are in a straight configuration and extend along the axis $A_1$.

In one embodiment, surgical fasteners are pre-loaded into the proximal shaft section 48 of the applicator instrument 40 and are advanced distally toward the distal end of the distal shaft section 50 each time the trigger 44 is squeezed. In one embodiment, during a single firing cycle, only the lead surgical fastener in the articulating shaft 46 is advanced into the distal shaft section 50 for being dispensed from the distal end of the distal shaft section 48. The trailing surgical fasteners remain in the proximal shaft section 48.

Figure 13A:
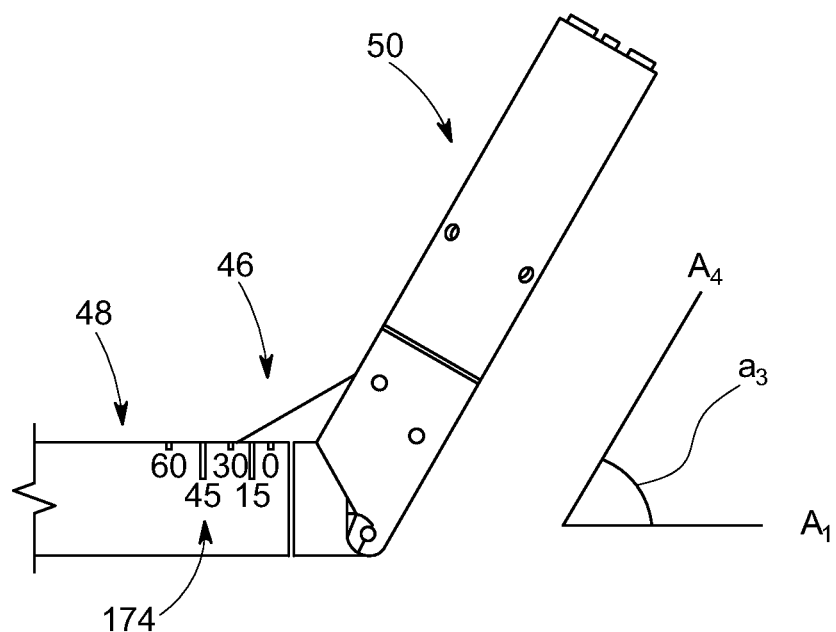
FIGS. 13A-13B show the distal end of the articulating shaft of the applicator instrument of FIG. 1 with the distal shaft section articulated at an angle relative to the proximal shaft section.
Figure 13B:
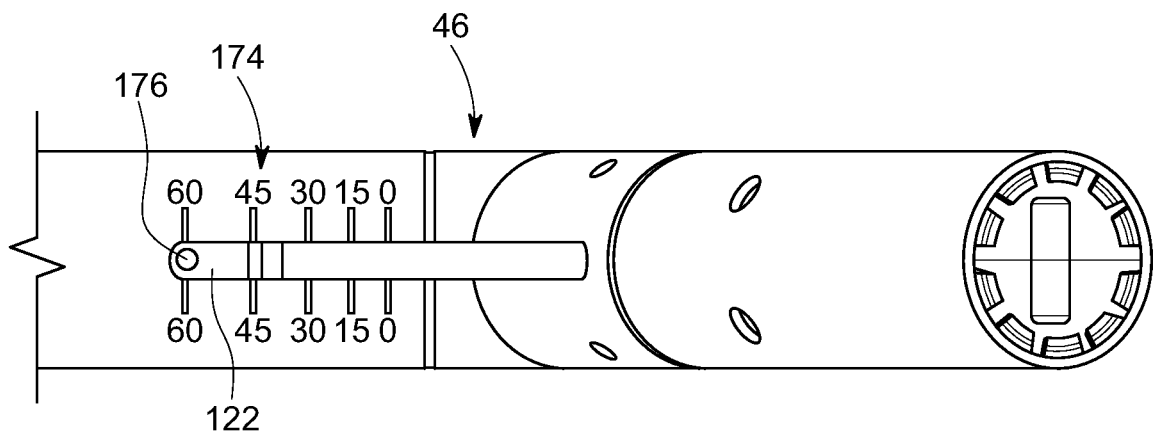

Referring to FIGS. 13A and 13B, in one embodiment, when the articulating shaft 46 is fully articulated, the angle marker 176 (FIG. 13B) on the proximal inner member 122 is aligned with 60 degrees on the angle indicia 174 to indicate that the distal shaft section 50 extends along an axis $A_4$ that defines an $\alpha_3$ angle of about 60 degrees with the proximal shaft section 48 that extends along axis $A_1$.

Figure 14:
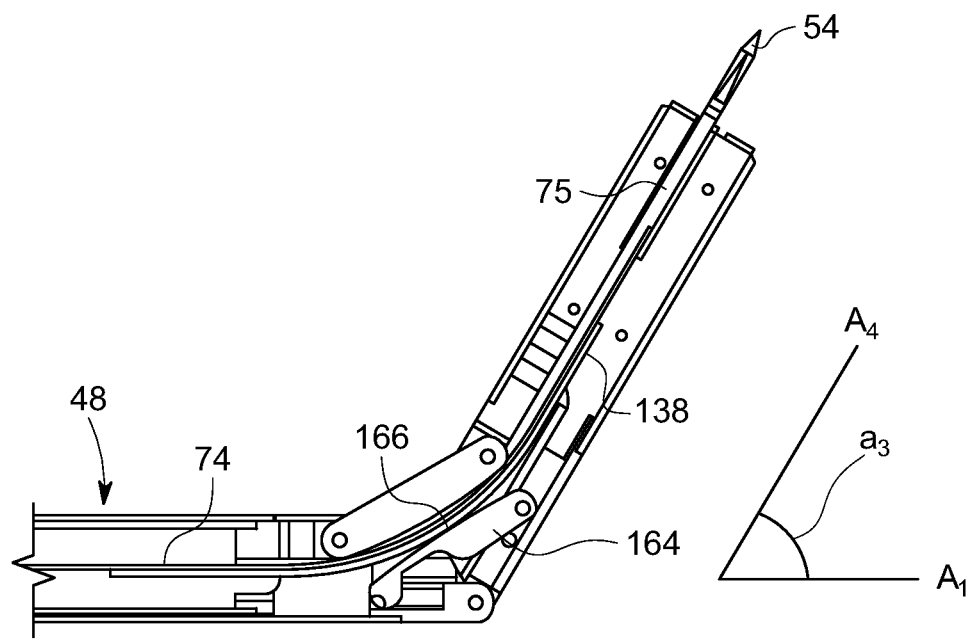
FIG. 14 shows a cross-sectional view of FIG. 13A-13B when dispensing a surgical fastener from a distal end of the articulating shaft, in accordance with one embodiment of the present invention.

FIG. 14 shows the curvature of the firing rod 74 and the incompressible member 138 to accommodate the 60 degree angle between the proximal shaft section 48 and the distal shaft section 50. The top surface 166 of the support member 164 functions as a floor support surface for the incompressible member 138 and the firing rod 74 so that the flexed elements do not kink or buckle when in the curved configuration. The support member 164 also supports the firing rod 174 during a firing cycle so that it may effectively transmit force to the insertion fork 75 for dispensing a surgical fastener 54.

Figure 15A:
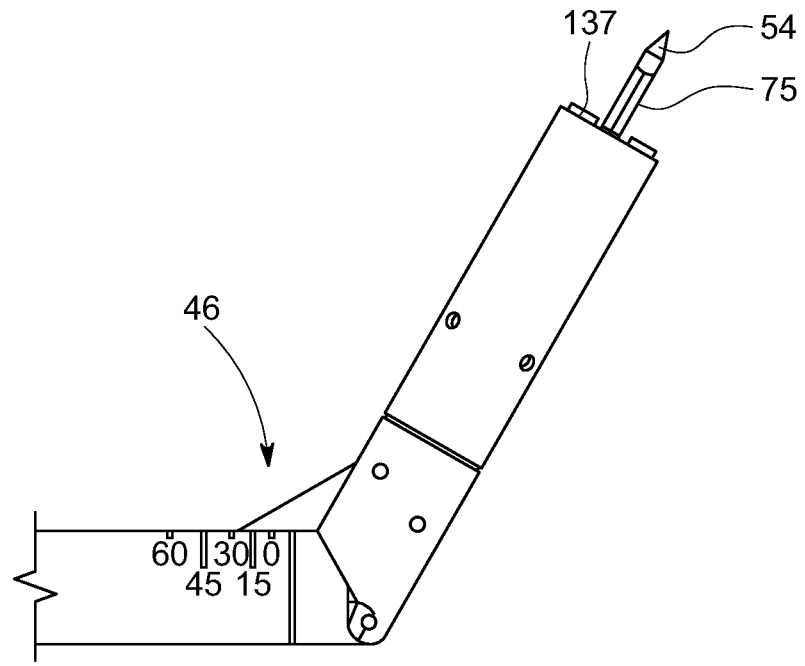
FIGS. 15A-15C show the articulating shaft of FIGS. 13A-13B when dispensing a surgical fastener from a distal end of the articulating shaft.
Figure 15B:
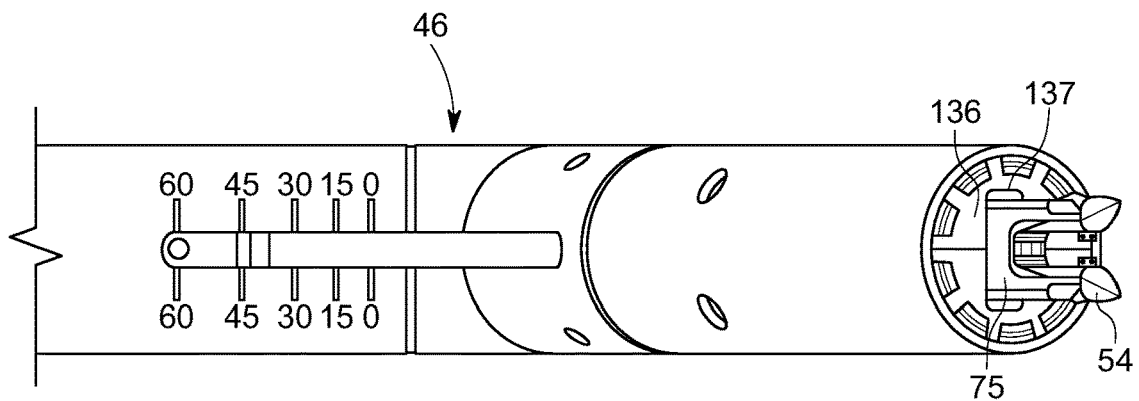
Figure 15C:
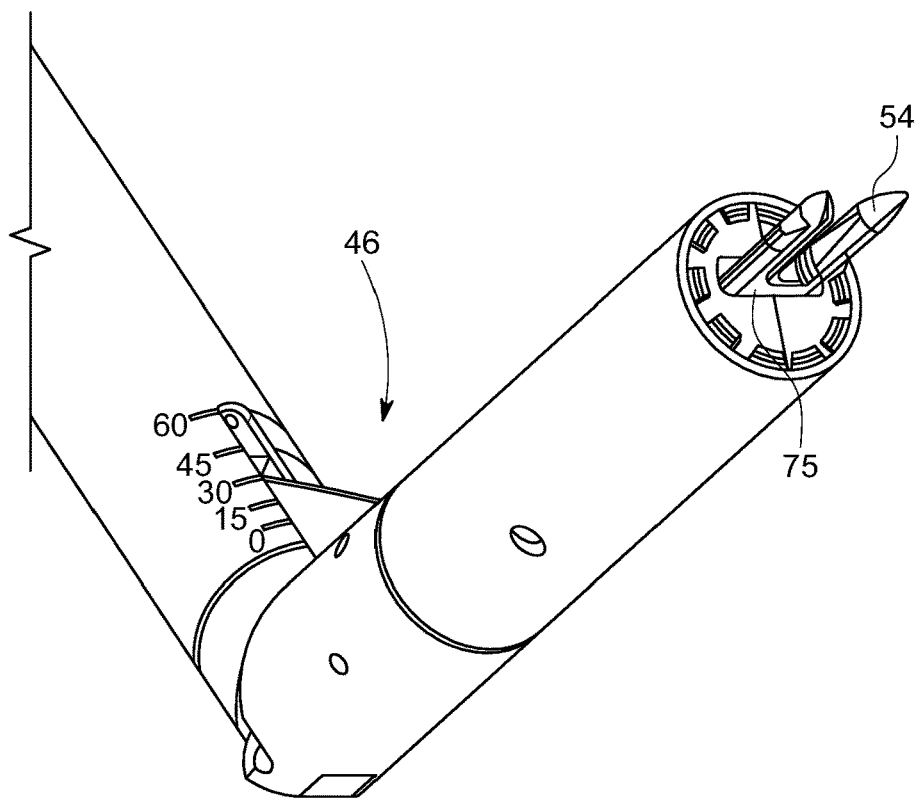

Referring to FIGS. 15A-15C, during a firing cycle, with the articulating shaft 46 fully articulated, the trigger 44 (FIG. 1) may be squeezed so that the firing system advances the insertion fork 75 a set distance beyond the distal end face 137 of the distal inner member 136 for dispensing a lead surgical fastener 54 from the distal end of the articulating shaft 46.

Figure 16:
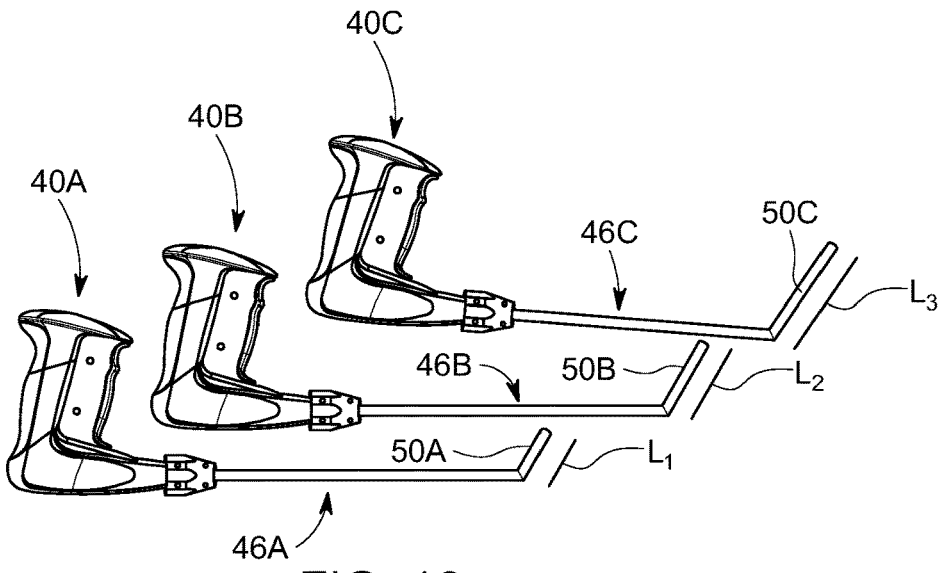
FIG. 16 shows applicator instruments having articulating shafts with distal shaft sections of varying lengths, in accordance with one embodiment of the present invention.

Referring to FIG. 16, in one embodiment, applicator instruments may include articulating shafts having distal shaft sections of different lengths. In one embodiment, a first applicator instrument 40A has an articulating shaft 46A with a distal shaft section 50A having a first length $L_1$. A second applicator instrument 40B has an articulating shaft 46B with a distal shaft section 50B having a second length $L_2$ that is greater than $L_1$. A third applicator instrument 40C has an articulating shaft 46C with a distal shaft section 50C having a third length $L_3$ that is greater than $L_2$. In one embodiment, a surgeon can select one of the applicator instruments 40A, 40B, 40C depending upon the surgical conditions that arise during a surgical procedure. The distal shaft length L may be in the range of about 0.25-5.0 inches.

Figure 17A:
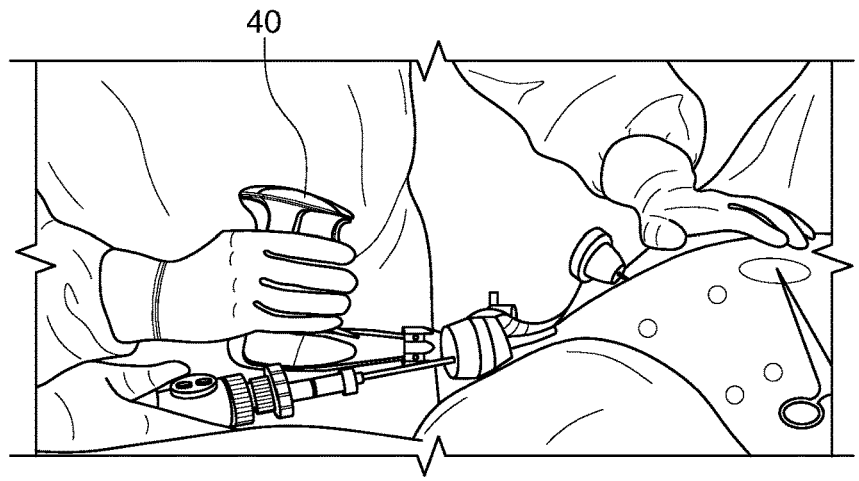
FIGS. 17A and 17B show the applicator instrument of FIG. 1 when being used on a patient during a surgical procedure.
Figure 17B:
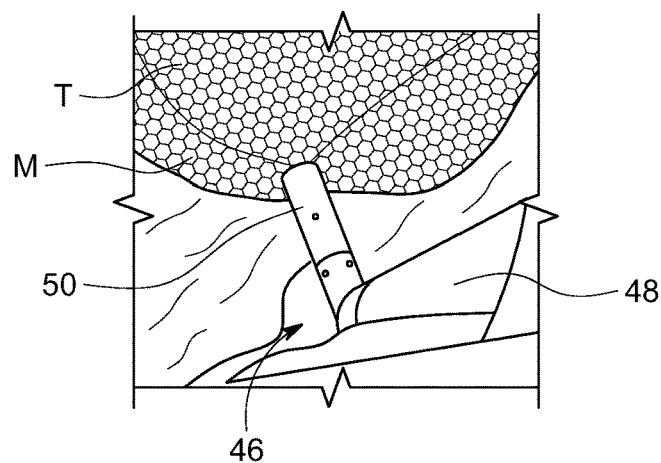

Referring to FIGS. 17A and 17B, during a surgical procedure, the articulating shaft 46 of the applicator instrument 40 is advanced through a cannula to a surgical site. The distal shaft section 50 may be articulated to an angle relative to the proximal shaft section 48 so that the distal end face of the distal shaft section is flush with a major surface of a surgical mesh M for securing the surgical mesh to underlying tissue T.

In one embodiment, a patient with a ventral or incisional hernia is prepared for a laparoscopic hernia repair procedure as set forth below. The patient is examined and the hernia location is identified using palpation or other methods. The patient is administered conventional general anesthesia in a conventional manner by induction and inhalation. A Veress needle is inserted into the abdominal cavity through the skin. A pneumoperitoneum of 8-15 mmHg is created. One 10 mm trocar is inserted in the left upper quadrant of the abdomen as far lateral as possible. A 30 degree laparoscopic camera is inserted through the trocar and the contents of the abdominal cavity are assessed. Two additional 5 mm trocars are placed caudal of the 10 mm port. Laparoscopic instruments are used to reduce the contents of hernia. The edges of the healthy fascia around the defect are examined and any attachments of viscera to the abdominal wall are divided to create a free space for fixation of the mesh. The size of the defect is assessed. In one embodiment, the defect may be primarily closed with sutures, if desired.

At this point in the procedure, the surgeon then prepares a mesh hernia patch. The mesh is sized to ensure adequate overlap beyond the margins of the defect on all sides. The mesh is rolled and inserted into the abdominal cavity through the 10 mm trocar. The mesh is unrolled and placed over the defect. Stay sutures may be placed through the mesh into the abdominal tissue as desired, i.e. at the four compass points of the mesh (North, South, East, West).

In one embodiment, an applicator instrument as disclosed herein, in the unarticulated configuration shown in FIG. 1, is inserted through one of the 5 mm trocars. As desired, the surgeon may articulate the distal end of the applicator instrument (FIGS. 7A-7B) to improve the access of the applicator instrument to the mesh placed adjacent to the abdominal wall. The distal end of the applicator instrument may be used to manipulate the mesh and place the mesh in a desired location prior to being fixated. In one embodiment, the applicator instrument is placed in an articulated configuration manipulating the ipsilateral edge of the mesh nearest to the trocar sites. Regardless of whether the applicator instrument is articulated or unarticulated, the trigger of the applicator instrument is deployed (e.g., squeezed) to deliver surgical fasteners through the mesh and into the abdominal wall. The perimeter of the mesh is fixated using a plurality of surgical fasteners in a crown configuration. For each firing of the applicator instrument, the applicator instrument may be articulated or unarticulated, as appropriate for the target location of the fastener. In one embodiment, an inner crown of surgical fasteners may also be applied, if desired. In one embodiment, the surgeon may unarticulate and move the applicator instrument to one of the other trocars, if desired.

The mesh repair is inspected to ensure it is sufficiently fixated to the abdominal wall. The applicator instrument is unarticulated and removed from the trocar. The camera, laparoscopic instruments, and trocars are removed from the abdominal cavity. The trocar incisions may be closed using appropriate suturing or closure techniques. The patient is moved to a recovery room.

Figure 18A:
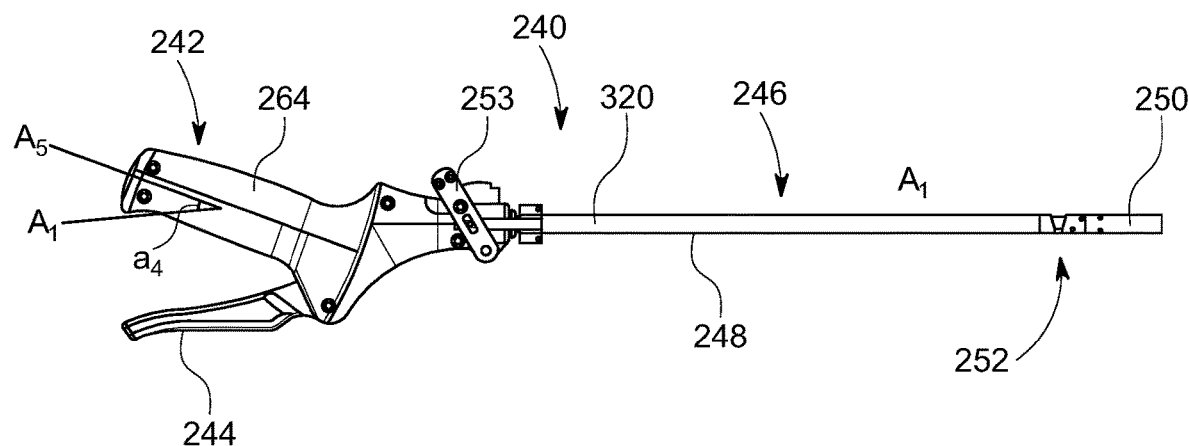
FIGS. 18A and 18B show an applicator instrument for dispensing surgical fasteners including a handle, an articulating shaft having a proximal shaft section and a distal shaft section, and an articulation control lever for controlling the articulation angle of a distal shaft section relative to the proximal shaft section, in accordance with one embodiment of the invention.
Figure 18B:
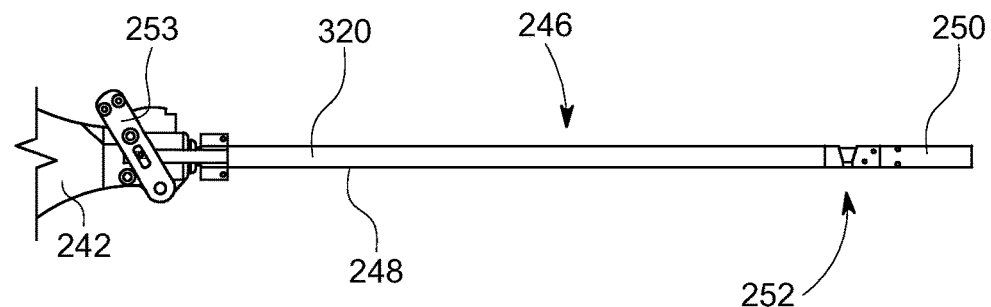

Referring to FIGS. 18A and 18B, in one embodiment, an applicator instrument 240 for surgical fasteners preferably includes a handle 242 having a trigger 244 and an articulating shaft 246 having a proximal shaft section 248, a distal shaft section 250, and an articulating joint 252 located between the proximal and distal shaft sections. The handle 242 includes a hand grip 264 that opposes the trigger 244. The hand grip 264 extends along an axis $A_5$ that defines an acute angle $\alpha_4$ of about 20 degrees relative to the longitudinal axis $A_1$ of the proximal shaft section 248. The applicator instrument 240 includes an articulation control lever 253 that is located at a distal end of the handle 242, which may be toggled between different positions for changing the angle of the distal shaft section 250 relative to the proximal shaft section 248. In one embodiment, the articulation control lever 253 is coupled with the proximal end of a proximal outer tube 320 for sliding the proximal outer tube in distal and proximal directions along the axis $A_1$.

Figure 19A:
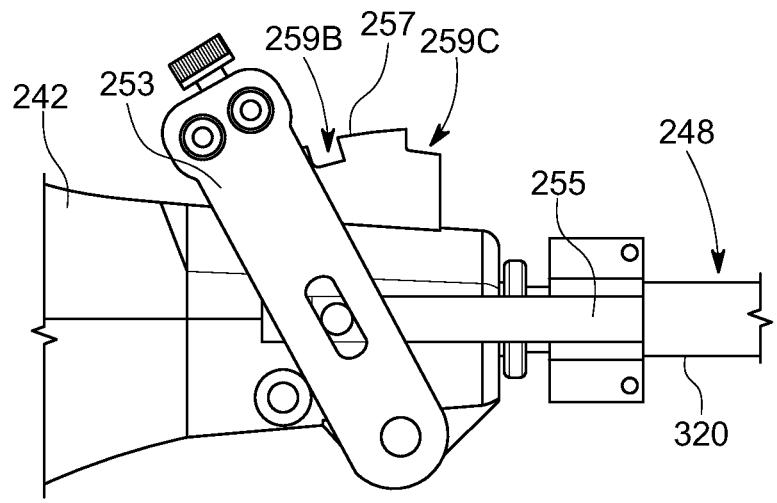
FIGS. 19A-19C show the articulation control lever of FIGS. 18A and 18B is a first position so that the distal shaft section and the proximal shaft section are in the straight, non-articulated configuration shown in FIGS. 18A and 18B.
Figure 19B:
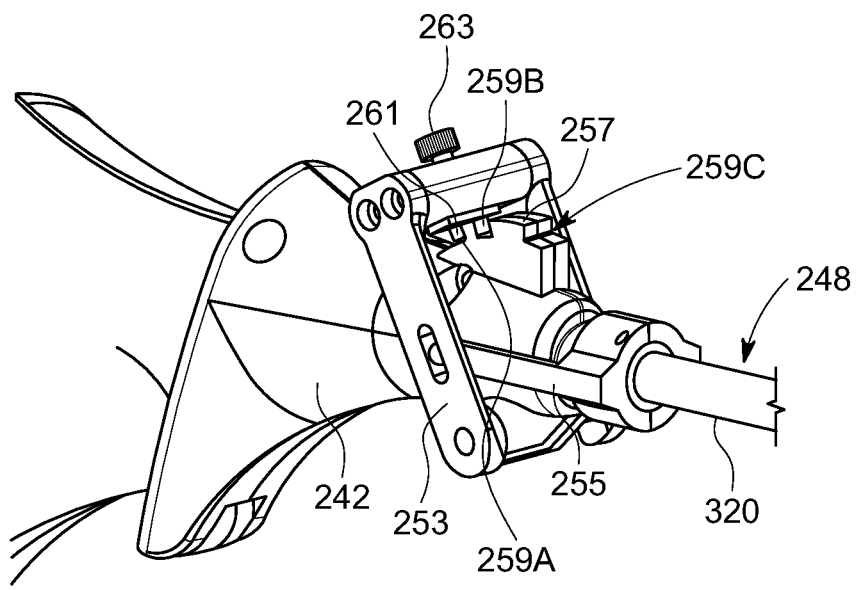
Figure 19C:
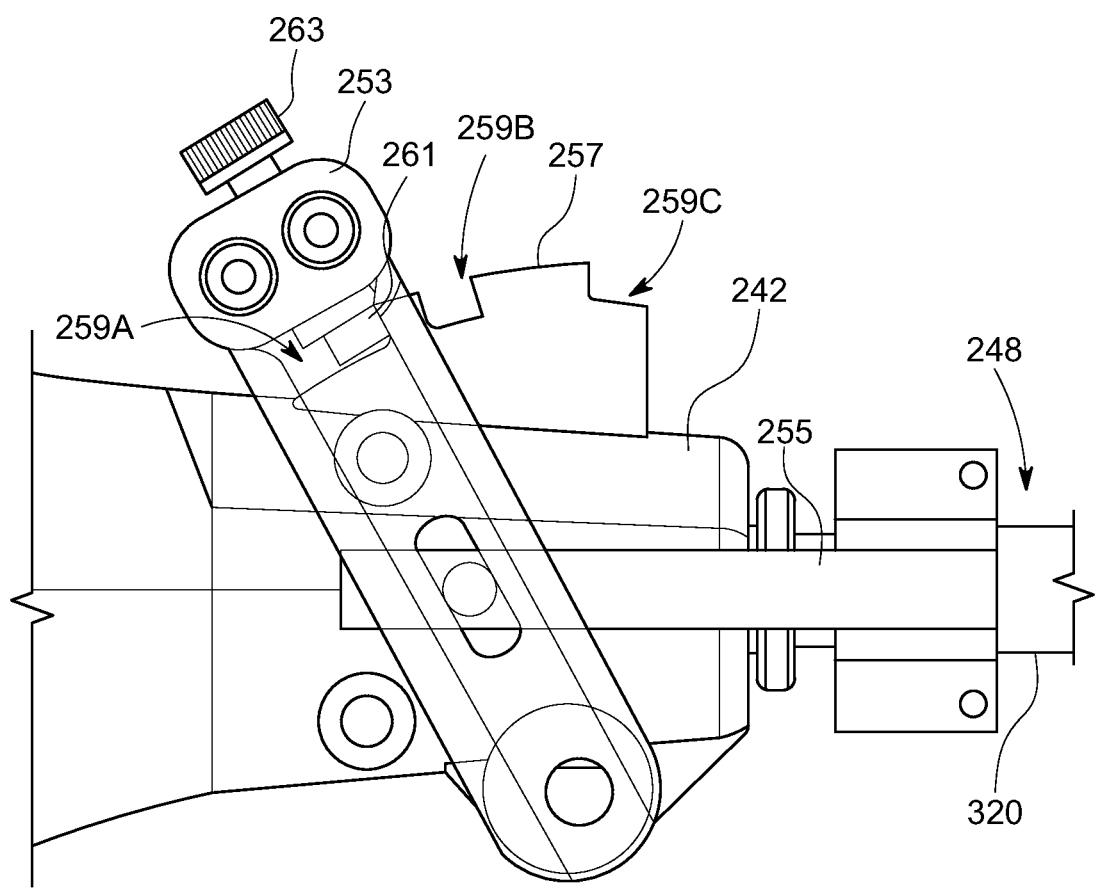

Referring to FIGS. 19A-19C, in one embodiment, the articulation control lever 253 is coupled with a sliding member 255 that, in turn, is coupled with the proximal end of the proximal outer tube 320 of the proximal shaft section 248. In one embodiment, as the lever 253 moves distally, the proximal outer tube 320 slides distally away from the handle 242, and as the lever 253 moves proximally, the proximal outer tube 320 slides proximally toward the handle 242.

In one embodiment, the articulation control lever 253 engages with a cam surface 257 having spaced detents 259A-259C associated with different articulation angles (e.g., 0, 30, 60 degrees). Rather than providing an articulation control element that is infinitely adjustable to different articulation angles, the articulation control lever provides articulation to certain predetermined angles that are typically used or are preferred by surgeons.

In one embodiment, the articulation control lever 253 preferably includes a spring loaded lock 261 that is coupled with a lock release knob 263. In one embodiment, the lock release knob 263 is engaged for retracting the spring loaded lock 261 so that the lever 253 may be moved between the spaced detents 259A-259C for setting an articulation angle for the distal shaft section 250 relative to the proximal shaft section 248 (FIG. 18A).

Figure 20:
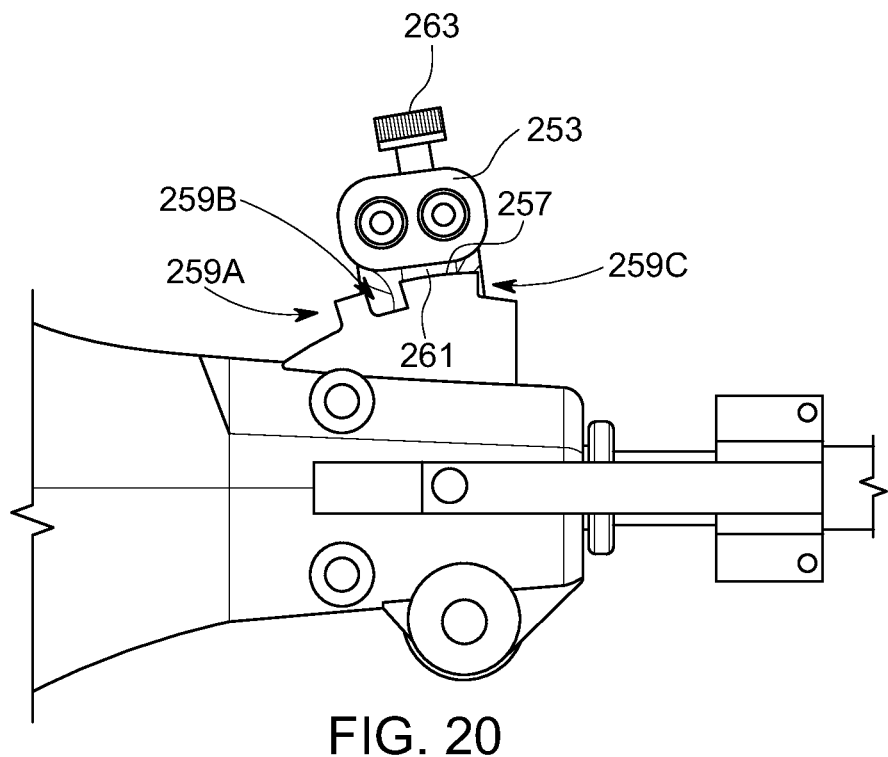
FIG. 20 shows a side view of the articulation control lever of FIGS. 19A-19C with the lever between a second position and a third position for changing the angle of the distal shaft section relative to the proximal shaft section.
Figure 21A:
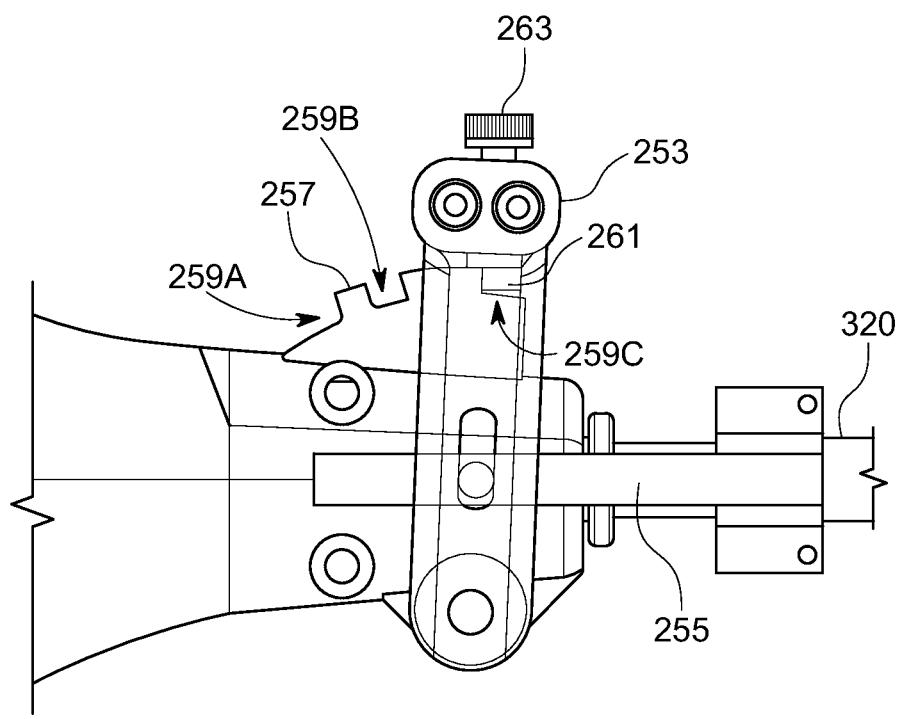
FIGS. 21A-21C show the articulation control lever of FIGS. 19A-19C in a third position for angling the distal shaft section relative to the proximal shaft section.
Figure 21B:
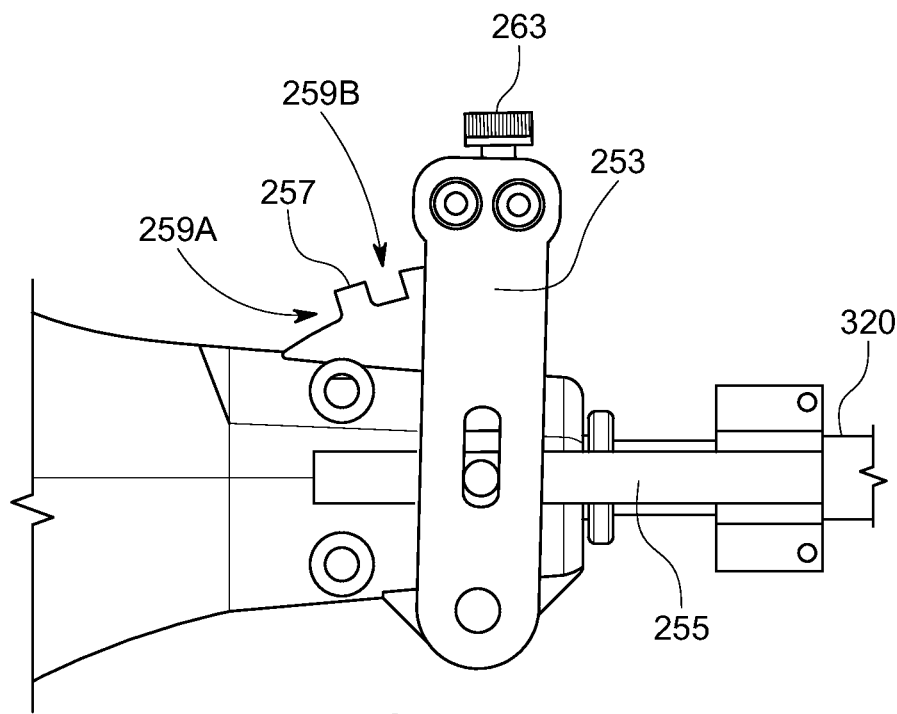
Figure 21C:
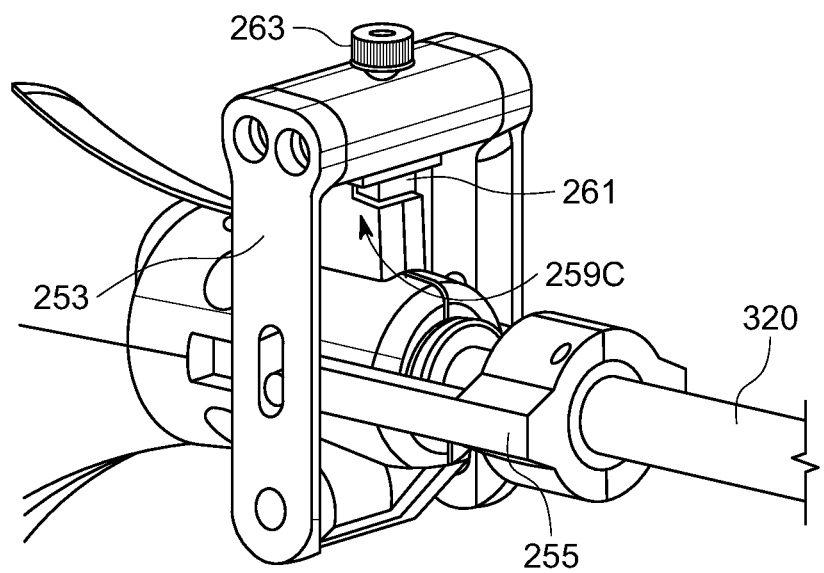

FIG. 20 shows the articulation control lever 253 located between the second spaced detent 259B associated with a 30 degree angle and the third spaced detent 259C associated with a 60 degree angle. The lock release knob 263 and the spring loaded lock 261 have been retracted so that the spring loaded lock 261 may slide over the cam surface 257 between the second spaced detent 259B and the third spaced detent 259C. Referring to FIGS. 21A-21C, when the lever 253 has been fully advanced to the distal-most position, the lock release knob 263 and the spring loaded lock 261 are extended for locking the lever 253 at the position aligned with the third spaced detent 259C (e.g., the 45 degree position). The sliding member 255 and the proximal outer tube 320 are locked from sliding movement along the axis $A_1$ as long as the lever 253 is locked in place in one of the spaced detents 259A-259C by the spring loaded lock 261.

Figure 22A:
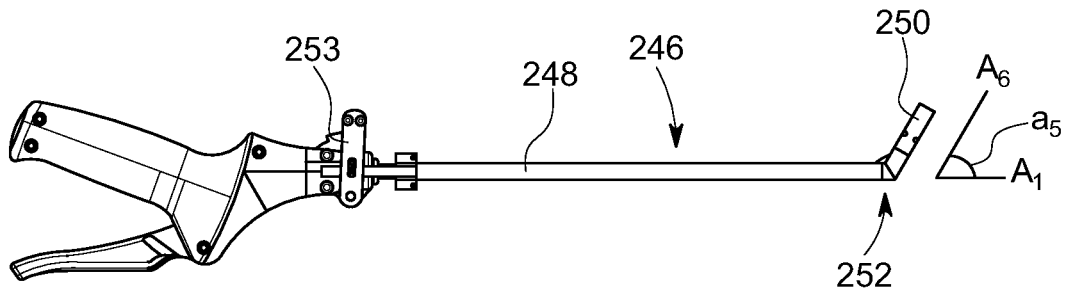
FIGS. 22A-22C show the applicator instrument of FIGS. 18A and 18B with the distal shaft section articulated at an angle relative to the proximal shaft section.
Figure 22B:
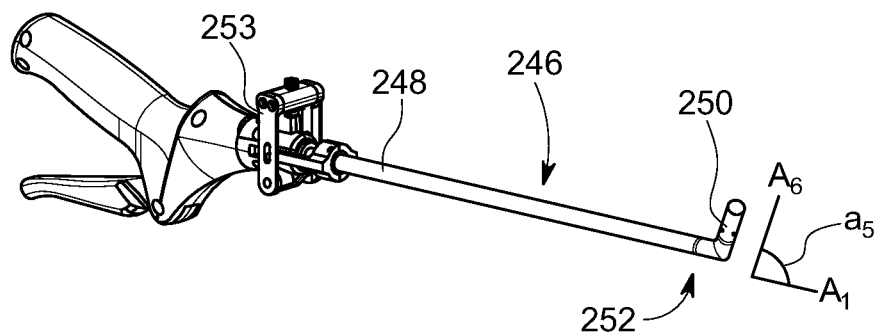
Figure 22C:
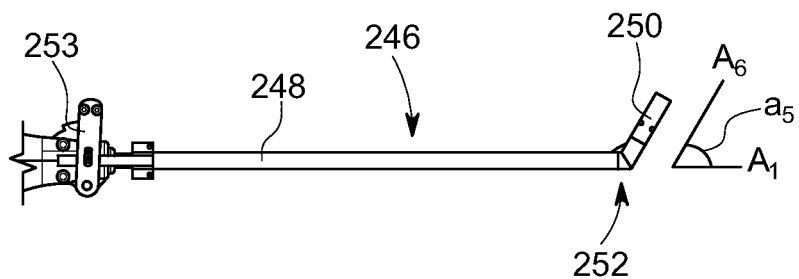

Referring to FIGS. 22A-22C, in one embodiment, when the articulation control lever 253 is advanced to the distal-most toggle position, the distal shaft section 250 pivots about the articulation joint 252 so that the distal shaft section 250 extends along an axis A6 that defines an angle α5 of about 60 degrees relative to the longitudinal axis A1 of the proximal shaft section 248.

Figure 23:
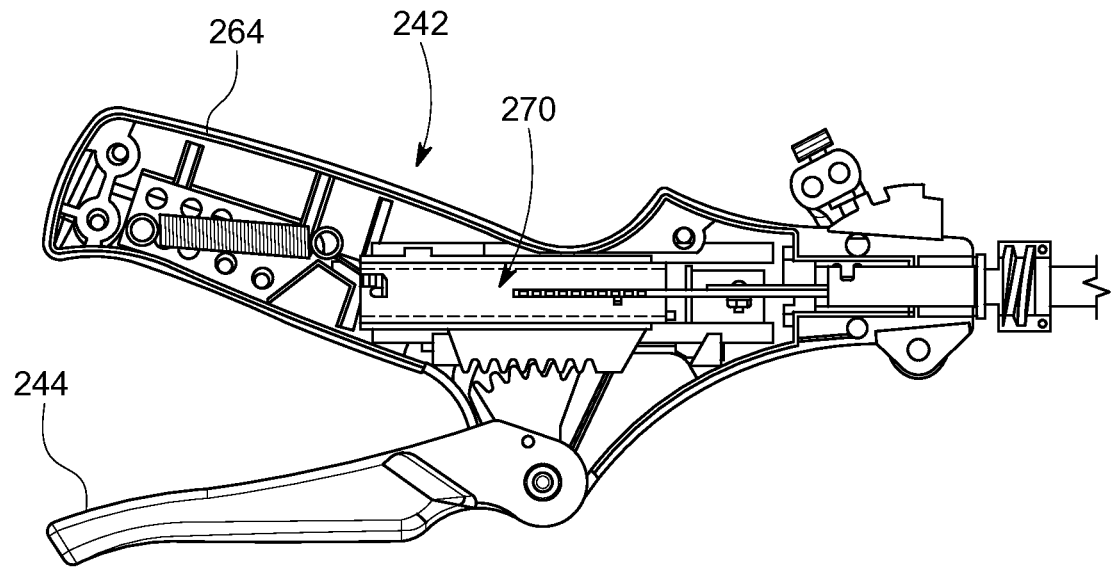
FIG. 23 shows a cross-sectional view of the handle and firing system of the applicator instrument shown in FIGS. 18A and 18B.
Figure 24A:
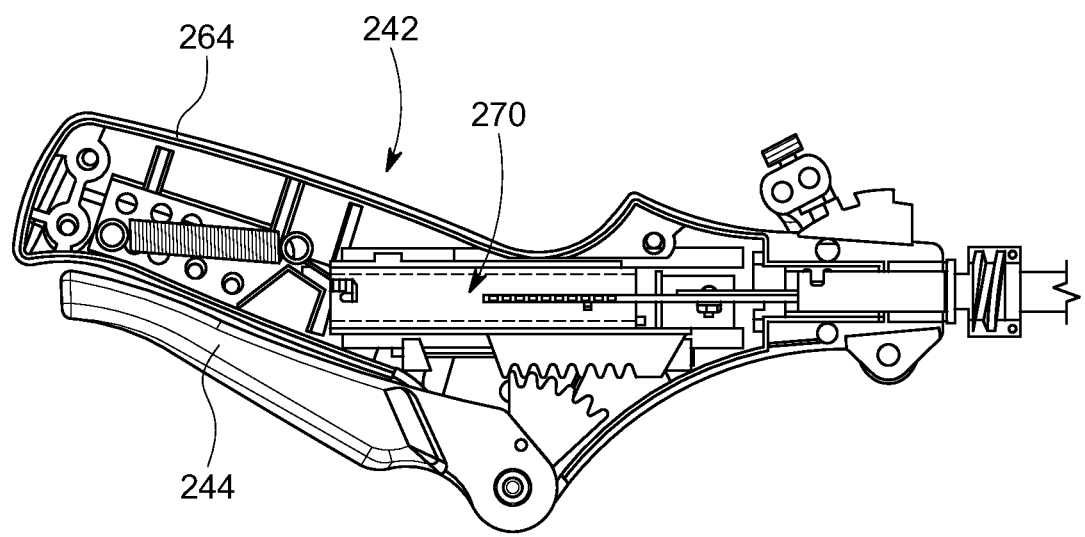
FIGS. 24A and 24B show the handle and the firing system of FIG. 23 during a firing cycle for dispensing a surgical fastener.
Figure 24B:
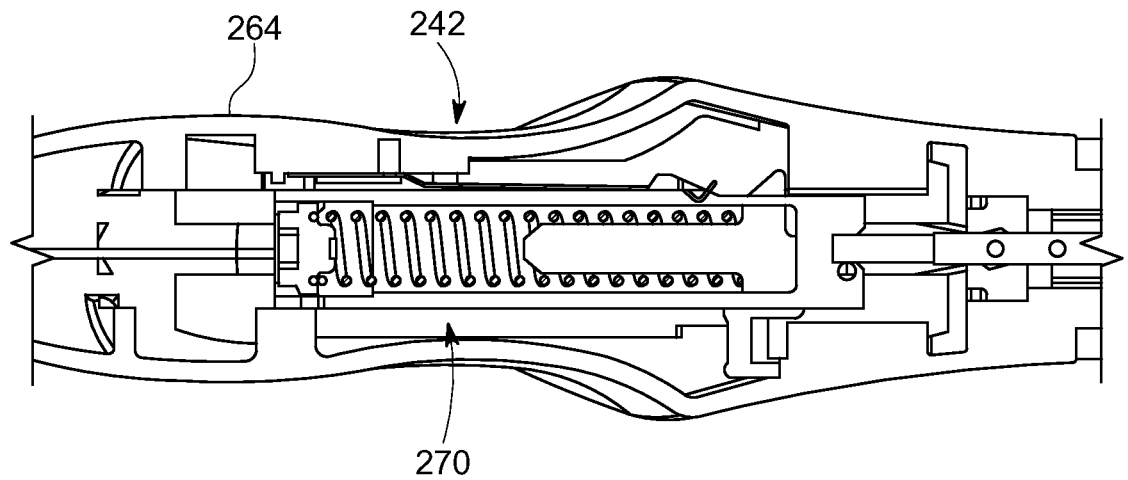

Referring to FIG. 23, in one embodiment, the applicator instrument 240 includes a stored energy firing system 270 that is disposed inside the handle 242. The firing system 270 includes one or more of the elements and operates as disclosed herein and as described in commonly assigned U.S. Pat. Nos. 8,579,920; 8,728,098; 8,728,099; 8,894,669; and 8,920,439, the disclosures of which are hereby incorporated by reference herein. Referring to FIGS. 23 and 24A-24B, the firing system 270 dispenses a single surgical fastener from the distal end of the shaft each time the trigger 244 is squeezed toward the hand grip 264 of the handle 242.

Figure 25:
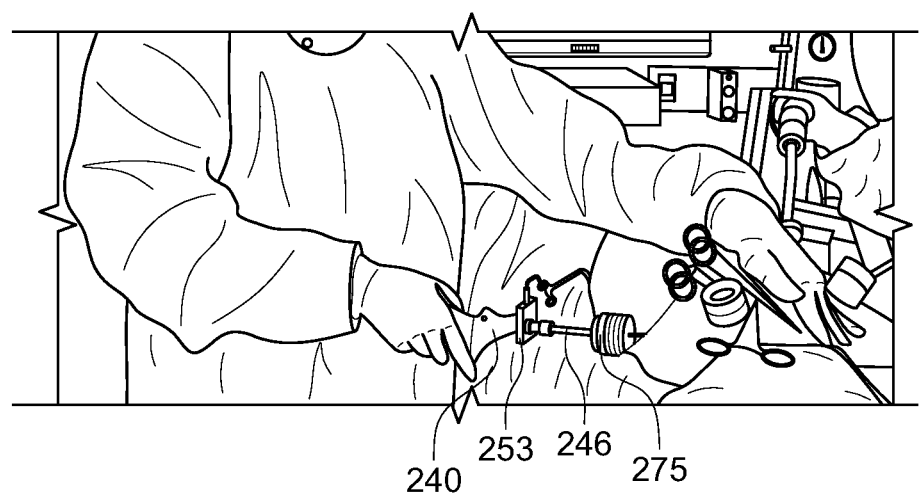
FIG. 25 shows a medical procedure using the applicator instrument shown in FIGS. 18A and 18B.

Referring to FIG. 25, during a surgical procedure, the articulating shaft 246 of the applicator instrument 240 may be advanced through a cannula 275 and to a surgical site for dispensing surgical fasteners at the surgical site. The articulation control lever 253 may be engaged by a surgeon for changing the angle of the distal shaft section relative to the proximal shaft section.

Figure 26A:
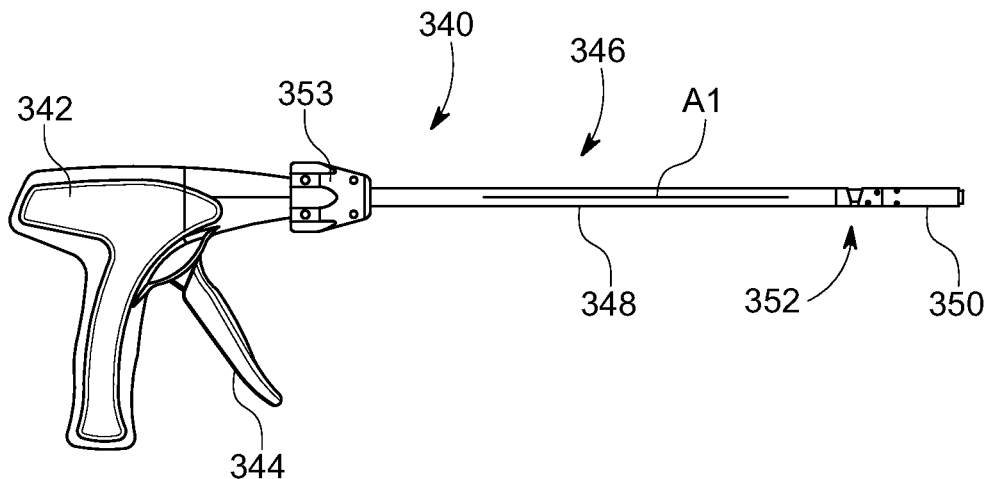
FIGS. 26A and 26B show an applicator instrument for dispensing surgical fasteners including a handle, an articulating shaft having a proximal shaft section and a distal shaft section, and an articulation control knob for controlling the articulation angle of a distal shaft section relative to the proximal shaft section, in accordance with one embodiment of the invention.
Figure 26B:
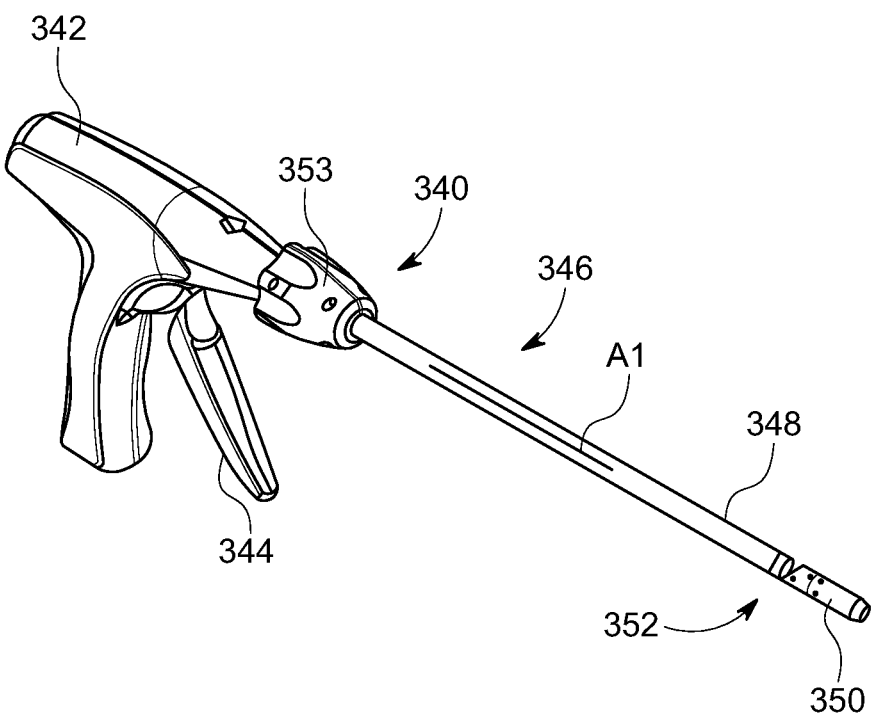

Referring to FIGS. 26A and 26B, in one embodiment, an applicator instrument 340 for dispensing surgical fasteners includes a handle 342 having a trigger 344, and an articulating shaft 346 with a proximal shaft section 348 and a distal shaft section 350 that articulates relative to the proximal shaft section. The distal shaft section 350 is moveable between a first position in which it extends along a longitudinal axis $A_1$ of the proximal shaft section 348 and an articulated configuration in which it is positioned at different angles relative to the longitudinal axis $A_1$ of the proximal shaft section 348. In one embodiment, a distal end of the proximal shaft section 348 is pivotally connected with a proximal end of the distal shaft section 350 via an articulating joint 352, which enables the distal shaft section 350 to articulate to different angles relative to the longitudinal axis $A_1$ of the proximal shaft section 348. The applicator instrument has an articulation control knob 353 that is rotated for changing the articulation angle between the distal shaft section 350 and the proximal shaft section 348. In one embodiment, rotating the articulation control knob in a first direction increases the articulation angle and rotating the articulation control knob in an opposite, second direction reduces the articulation angle. In one embodiment, the articulation control knob 353 may be used to set the distal shaft section 350 at an infinite number of angles between about 0-60. In one embodiment, the articulation angle may be as great as 80 degrees. In FIGS. 26A and 26B, the articulating shaft 346 is straight so that the proximal shaft section 348 and the distal shaft section 350 both extend along the longitudinal axis $A_1$.

Figure 27A:
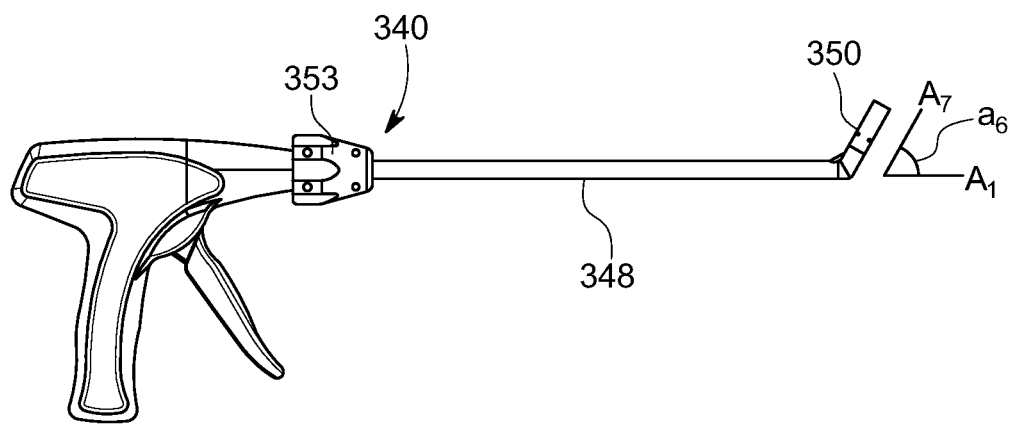
FIGS. 27A and 27B show the applicator instrument of FIGS. 26A and 26B with the distal shaft section articulated at an angle relative to the proximal shaft section.
Figure 27B:
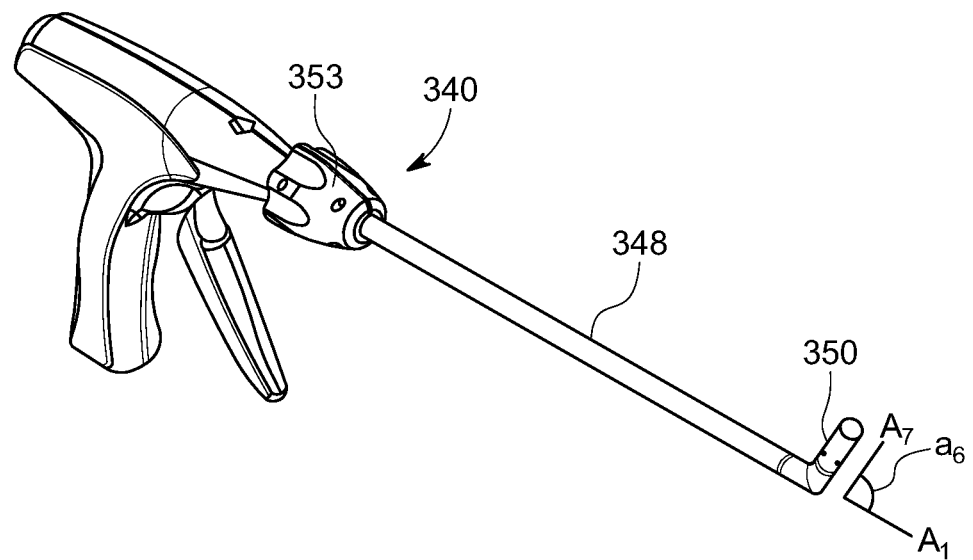

In one embodiment the articulation control knob 353 of the applicator instrument 340 is engaged for articulating the distal shaft section 350 relative to the proximal shaft section 348. Referring to FIGS. 27A and 27B, in one embodiment, the articulation control knob 353 is engaged so that distal shaft section 350 extends along an axis $A_7$ and the proximal shaft section 348 extends along the axis $A_1$ that defines an angle $\alpha_6$ of about 60 degrees. In one embodiment, the distal shaft section 50 moves between 0-60 degrees relative to the longitudinal axis $A_1$ of the proximal shaft section 48. In one embodiment, the articulation control knob 53 may be used to change the articulation angle of the distal shaft section 50 to any angle between 0-80 degrees.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An applicator instrument for dispensing surgical fasteners comprising:
    a handle;
    an articulating shaft extending from said handle, said articulating shaft including a proximal shaft section having a longitudinal axis, a distal shaft section, and an articulating joint interconnecting said proximal and distal shaft sections;
    said proximal shaft section including a proximal outer tube and a proximal inner member disposed inside said proximal outer tube, wherein said proximal inner member is stationary and said proximal outer tube slides along the longitudinal axis in distal and proximal directions relative to said proximal inner member;
    said distal shaft section including a distal outer tube and a distal inner member disposed inside said distal outer tube, wherein said distal outer tube is adapted to slide distally and proximally relative to said distal inner member;
    an incompressible member interconnecting said proximal inner member and said distal inner member to form an inner shaft member having a length extending along a longitudinal axis of said inner shaft member;
    an articulation control element coupled with said proximal outer tube for moving said proximal outer tube along the longitudinal axis in the distal and proximal directions, wherein distal movement of said proximal outer tube relative to said proximal inner member is configured to articulate said distal shaft section relative to said proximal shaft section via said articulating joint, wherein as said articulating shaft moves between a straight configuration and an articulated configuration the distance between a distal-most end of said distal outer tube and said handle changes while the length of said inner shaft member extending along the longitudinal axis of said inner shaft member remains fixed.

2. The applicator instrument as claimed in claim 1, wherein said articulating joint comprises a first pivot connection between a distal end of said proximal outer tube and a proximal end of said distal outer tube.

3. The applicator instrument as claimed in claim 2, wherein said articulating joint further comprises a joining member having a second pivot connection with said proximal inner member and a third pivot connection with said distal outer tube.

4. The applicator instrument as claimed in claim 3, wherein said proximal and distal inner members have longitudinally extending openings formed therein, and wherein said applicator instrument further comprises a firing rod adapted to move distally and proximally through the longitudinally extending openings formed in said proximal and distal inner members.

5. The applicator instrument as claimed in claim 4, further comprising:
    a firing system disposed in said handle and coupled with said firing rod;
    an actuator coupled with said firing system for commencing a firing cycle of said firing system.

6. The applicator instrument as claimed in claim 5, further comprising a plurality of surgical fasteners disposed within said articulating shaft, wherein a leading one of said surgical fasteners is dispensed during each said firing cycle of said firing system.

7. The applicator instrument as claimed in claim 6, wherein said incompressible member and said firing rod are flexible for bending when said distal shaft section is articulated relative to said proximal shaft section.

8. The applicator instrument as claimed in claim 7, wherein said incompressible member and said firing rod are straight when said articulating shaft is in the straight configuration and are curved when said articulating shaft is in the articulated configuration.

9. The applicator instrument as claimed in claim 8, further comprising a firing rod support located between said firing rod and said first pivot connection, said firing rod support having a support surface for supporting an outer curved surface of said firing rod when said distal shaft section is articulated relative to said proximal shaft section.

10. The applicator instrument as claimed in claim 9, wherein said incompressible member is located between said firing rod and said support surface of said firing rod support.

11. The applicator instrument as claimed in claim 1, wherein said incompressible member maintains a constant distance between a distal end face of said distal inner member and a proximal end of said proximal inner member as said articulating shaft moves between the straight configuration and the articulated configuration.

12. The applicator instrument as claimed in claim 3, further comprising:
a first slot formed in a top side of said proximal outer tube;
a second slot formed in a top side of said distal outer tube that is aligned with the first slot formed in the top side of said proximal outer tube, wherein said joining member passes through said aligned first and second slots when said distal shaft section is articulated relative to said proximal shaft section.

13. The applicator instrument as claimed in claim 12, further comprising:
said proximal inner member having a marker provided on a top surface thereof that is visible through said first slot formed in the top side of said proximal outer tube, wherein during articulation of said distal shaft section relative to said proximal shaft section said proximal outer tube moves relative to said marker on said proximal inner member for indicating the angle of articulation of said distal shaft section relative to said proximal shaft section.

14. An applicator instrument for dispensing surgical fasteners comprising:
a handle;
an articulating shaft extending from said handle, said articulating shaft including a proximal shaft section extending along a longitudinal axis, a distal shaft section, and an articulating joint interconnecting said proximal and distal shaft sections;
said proximal shaft section including a proximal outer tube that slides in distal and proximal directions along the longitudinal axis and a proximal inner member disposed inside said proximal outer tube that is stationary and that is secured to said handle;
said distal shaft section including a distal outer tube and a distal inner member disposed inside said distal outer tube, wherein said distal outer tube is adapted to slide distally and proximally relative to said distal inner member;
an articulation control element coupled with said articulating shaft for changing the articulation angle of said distal shaft section relative to said proximal shaft section; and
an incompressible member interconnecting said proximal inner member and said distal inner member to form an inner shaft member having a length extending along a longitudinal axis of said inner shaft member, wherein as said articulating control element moves said articulating shaft between a straight configuration and an articulated configuration the length of said inner shaft member remains fixed.

15. The applicator instrument as claimed in claim 14, further comprising:
a firing system disposed within said handle, said firing system including a firing rod that extends through said proximal and distal inner members;
an actuator coupled with said firing system for commencing a firing cycle of said firing system; and
surgical fasteners disposed within said articulating shaft, wherein a leading one of said surgical fasteners is dispensed during each said firing cycle of said firing system.

16. The applicator instrument as claimed in claim 15, wherein said articulating joint comprises:
a first pivot connection between a distal end of said proximal outer tube and a proximal end of said distal outer tube; and
a joining member having a proximal end forming a second pivot connection with said proximal inner member and a distal end forming a third pivot connection with said distal outer tube.

17. The applicator instrument as claimed in claim 16, wherein a distance between a distal-most end of said distal outer tube and a distal end of said handle changes as said articulating shaft moves between a straight configuration and an articulated configuration, and wherein said incompressible member and said firing rod are flexible for bending when said distal shaft section is articulated relative to said proximal shaft section.

18. The applicator instrument as claimed in claim 17, further comprising a firing rod support located between said firing rod and said first pivot connection, said firing rod support having a support surface for supporting an outer curved surface of said firing rod when said distal shaft section is articulated relative to said proximal shaft section, wherein said incompressible member is located between said firing rod and said support surface of said firing rod support.

19. An applicator instrument for dispensing surgical fasteners comprising:
an articulating shaft including a proximal shaft section extending along a longitudinal axis, a distal shaft section, and an articulating joint interconnecting said proximal and distal shaft sections;
said proximal shaft section including a proximal outer tube that slides in distal and proximal directions along the longitudinal axis and a proximal inner member disposed inside said proximal outer tube that is stationary;
said distal shaft section including a distal outer tube and a distal inner member disposed inside said distal outer tube, wherein said distal outer tube is adapted to slide distally and proximally relative to said distal inner member;
an articulation control element coupled with said articulating shaft for changing the articulation angle of said distal shaft section relative to said proximal shaft section; and
an incompressible member interconnecting said proximal inner member and said distal inner member to form an inner shaft member having a length extending along a longitudinal axis of said inner shaft member, wherein as said articulating shaft moves between a straight configuration and an articulated configuration the distance between a distal-most end of said distal outer tube and a proximal end of said applicator instrument is configured to change while the length of said inner shaft member extending along the longitudinal axis of said inner shaft member remains fixed.

20. The applicator instrument as claimed in claim 19, further comprising:
- a housing connected with a proximal end of said articulating shaft, wherein said housing has a distal end that is rigidly secured to a proximal end of said proximal inner member;
- a firing system disposed within said handle, said firing system including a firing rod extending through said articulating shaft;
- an actuator coupled with said firing system for activating said firing system.

* * * * *